United States Patent [19]

Umetani et al.

[11] Patent Number: 5,196,531
[45] Date of Patent: Mar. 23, 1993

[54] POLY(N-CYCLIC IMINOETHER), PROCESS FOR PRODUCTION THEREOF, THERMOSETTING COMPOSITION CONTAINING IT AND THERMOSET RESIN

[75] Inventors: Hiroyuki Umetani; Hiroshi Mera; Hiroo Inata; Shunichi Matsumura, all of Iwakuni, Japan

[73] Assignee: Teijin Limited, Osaka, Japan

[21] Appl. No.: 929,496

[22] Filed: Aug. 18, 1992

Related U.S. Application Data

[63] Continuation of Ser. No. 382,584, Jul. 20, 1989, abandoned.

[30] Foreign Application Priority Data

Jul. 20, 1988 [JP] Japan ................................ 63-178961
Dec. 19, 1988 [JP] Japan ................................ 63-318475

[51] Int. Cl.$^5$ .................. C07D 263/00; C07D 265/04
[52] U.S. Cl. ........................................ 544/72; 548/233
[58] Field of Search ........................... 544/72; 548/233

[56] References Cited

U.S. PATENT DOCUMENTS

| Re. 28,669 | 12/1975 | Tomalia et al. | 544/72 |
|---|---|---|---|
| 3,563,920 | 2/1971 | Tomalia et al. | 544/72 |
| 3,639,395 | 2/1972 | Tomalia | 544/72 |
| 3,709,904 | 1/1973 | Tomalia et al. | 548/233 |
| 3,716,520 | 2/1973 | Tomalia | 544/72 |
| 3,723,451 | 3/1973 | Tomalia et al. | 544/72 |
| 3,763,177 | 10/1973 | Tomalia et al. | 544/72 |

FOREIGN PATENT DOCUMENTS 0273368 7/1988 European Pat. Off. .

Primary Examiner—Maurice J. Welsh
Assistant Examiner—Rabon Sergent
Attorney, Agent, or Firm—Sherman and Shalloway

[57] ABSTRACT

A novel poly(N-cyclic iminoether) compound and a process for production thereof which comprises (a) reacting a polyisocyanate compound with a haloalkyleneamine or (b) reacting a polyamine with an alkyl isocyanate, and then (c) cyclizing the resulting polyurea compound. Several thermosetting compositions containing the novel poly(N-cyclic iminoether) and thermoset resins therefrom are also proposed.

5 Claims, 18 Drawing Sheets

POLY(N-CYCLIC IMINOETHER), PROCESS FOR PRODUCTION THEREOF, THERMOSETTING COMPOSITION CONTAINING IT AND THERMOSET RESIN

This application is a continuation of application Ser. No. 07/382,584, filed Jul. 20, 1989, now abandoned.

BACKGROUND OF THE INVENTION

1. Field Of The Invention

This invention relates to a poly(N-cyclic iminoether), processes for production thereof, a thermosetting composition containing it, and a thermoset resin.

C-cyclic iminoether compounds, such as C-oxazoline and C-oxazine compounds, have previously been known, and used, for example, for modification of polyesters by reducing the amount of a terminal carboxylic acid or for improving polymer properties by chain extension. They are also used as materials for production of thermosetting resins by reaction with carboxylic acids, aromatic alcohol or aromatic amines.

2. Description Of The Prior Art

Japanese Laid-Open Patent Publications Nos. 40681/1988 and 26628/1989 disclose processes for producing a thermoset resin by heating (A) a poly(C-cyclic iminoether) having 2 to 4 cyclic iminoether groups in the molecule, (B) a polyepoxy compound and (C) a polyamine, an intramolecular acid anhydride and an aromatic polyhydroxy compound in the presence of an acid catalyst.

Japanese Laid-Open Patent Publication No. 33119/1989 discloses an epoxy curing agent comprising 0.05 to 0.2 mole of a C-oxazoline of the following formula

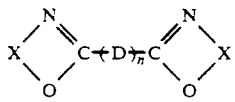

wherein
X represents a divalent organic group,
D represents a divalent organic group and n is 0 or 1, and 1 mole of an acid anhydride.

Japanese Laid-Open Patent Publication No. 104838/1987 discloses a process for producing a thermoset resin by reacting a 2,2'-(1,3-phenylene)bis(2-oxazoline) derivative with a compound selected from polycarboxylic acids, polyhydric alcohols and polyamines.

Japanese Laid-Open Patent Publication No. 75024/1988 discloses a thermosetting resin composition comprising (A) an epoxy compound, (B) a C-oxazoline compound, (C) a curing agent, for example a compound having a carboxyl, hydroxyl, acid anhydride or sulfonic group or an organosilane or organosiloxy compound, and as required, (D) a granular or fibrous filler.

U.S. Pat. No. 4,628,102 discloses the production of a compound containing both bicyclic amide acetal and epoxy functional groups by reacting a diepoxide compound and a mono(C-oxazoline).

U.S. Pat. No. 4,652,620 discloses the production of substantially insoluble and infusible crosslinked resinous compositions by reacting a mixture of a multifunctional epoxide, a phenolic compound and a compound containing at least two C-oxazoline groups in the melt phase.

Japanese Laid-Open Patent Publication No. 26627/1989 discloses the production of a thermoset resin by the reaction of a polyepoxide compound with a C-cyclic iminoether such as a C-oxazine or C-oxazoline.

Japanese Laid-Open Patent Publication No. 1533/1984 discloses a process for producing a thermoset resin which comprises reacting bis(C-oxazoline) compound and not more than 1 mole, per mole of the C-oxazoline compound, of a dicarboxylic acid under heat in the presence of a phosphite ester.

Japanese Laid-Open Patent Publication No. 146924/1988 discloses a process for producing a poly(e-theramide) which comprises copolymerizing C-oxazoline and a bis- or poly-phenolic compound in the presence of an alkali or alkaline earth metal cation complex (catalyst) at a temperature of 100° to 200° C.

Japanese Patent Publication No. 57330/1986 discloses a process for producing a C-oxazoline-modified unsaturated polyester which comprises reacting a C-oxazoline derivative having 1 to 4 oxazoline rings in the molecule with an unsaturated polyester having carboxyl groups. This publication states that the reaction is carried out at a temperature of 100° to 250° C. for about 10 minutes to 3 hours.

Japanese Laid-Open Patent Publication No. 48811/1989 discloses a thermosetting unsaturated polyester composition comprising an organic compound having a C-oxazoline ring and a boiling point of at least 140° C., an unsaturated polyester resin, reinforcing fibers such as glass fibers and a polymerization initiator (peroxide).

U.S. Pat. No. 4,551,511 discloses a process for preparing anhydride/styrene copolymers of higher molecular weight comprising heating a mixture of maleic anhydride, styrene and a small amount of C-oxazoline at a temperature in the range of from 50° C. to 150° C.

U.S. Pat. No. 4,351,936 discloses a process for producing a saturated polyester having a reduced terminal carboxyl group content, which comprises reacting a carboxyl-terminated saturated polyester with a monocyclic iminoether compound. The specification of this patent describes a mono N-, O- or C(0)-cyclic iminoether compound as the monocyclic iminoether compound.

SUMMARY OF THE INVENTION

It is a primary object of this invention to provide a novel poly(N-cyclic iminoether) compound having at least two N-cyclic iminoether rings in the molecule.

Another object of this invention is to provide a novel poly(N-cyclic iminoether) compound having higher reactivity than known C-oxazoline compounds.

Another object of this invention is to provide an industrially advantageous process for producing the poly(N-cyclic iminoether) compound of the invention.

Another object of this invention is to provide a novel thermosetting composition comprising the poly(N-cyclic iminoether) compound of the invention.

Another object of this invention is to provide a thermosetting composition having high reactivity, namely having the property of curing at a relatively low temperature and/or curing within a short period of time.

Another object of this invention is to provide a thermoset resin having a relatively high heat distortion temperature and a thermosetting resin which gives the thermoset resin.

Another object of the invention is to provide a low-shrinkage thermosetting composition which shrinks little during heat curing reaction (this property may be referred to hereinafter as "molding shrinkage"), namely in which the shrinkage at the time of converting the monomer to a cured polymer is low.

Further objects of the invention along with its advantages will become apparent from the following description.

BRIEF DESCRIPTION OF THE DRAWING FIGURES

DETAILED DESCRIPTION OF THE INVENTION

Figure 1:
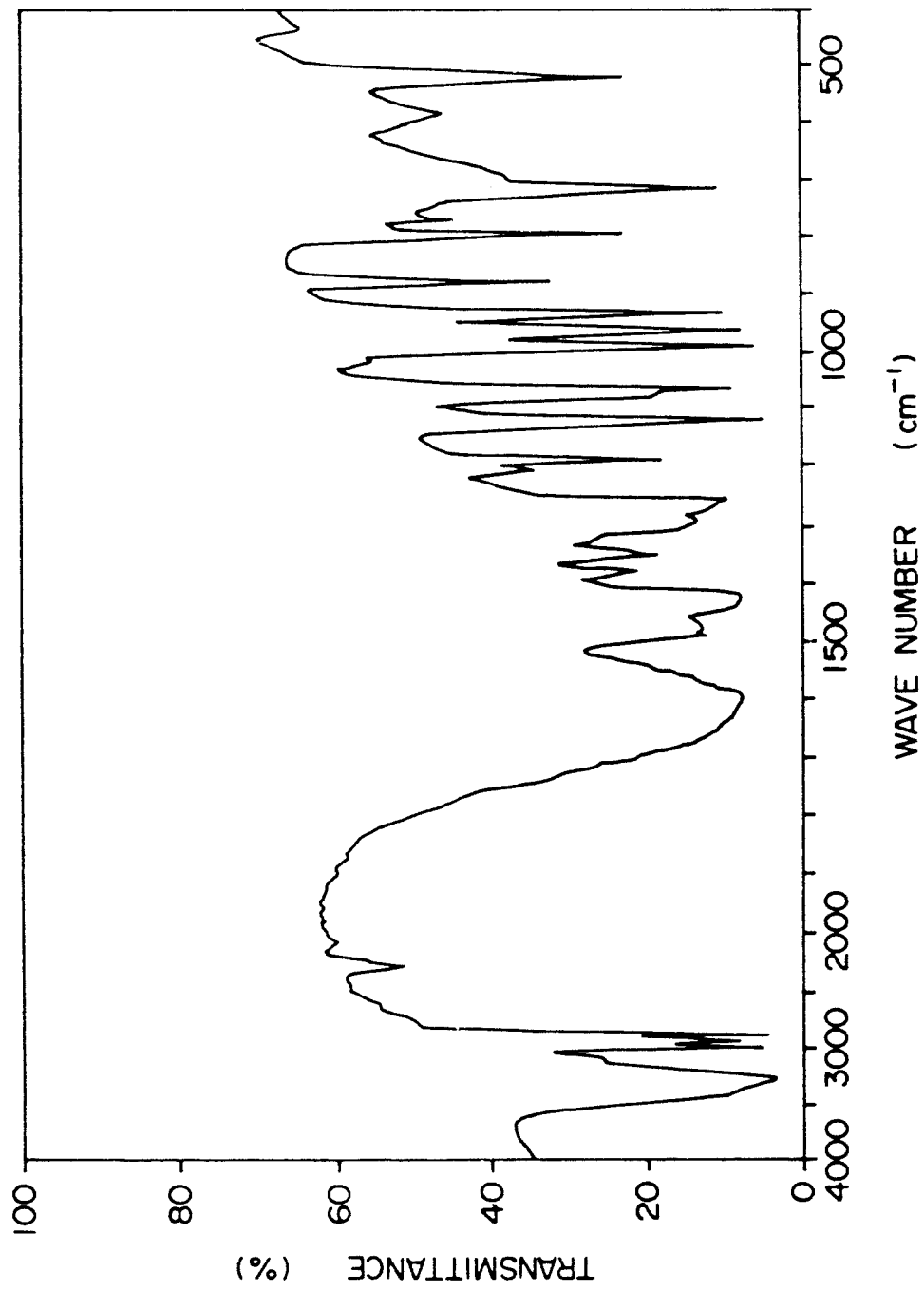
FIG. 1 is an IR spectra of the product produced by Example 1A.

The objects and advantages of this invention are firstly achieved by a poly(N-cyclic iminoether) compound represented by the following formula (I)

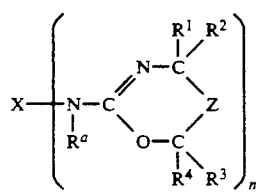

wherein
n is an integer of 2 to 10,

X is an n-valent hydrocarbon group which may be interrupted by a hetero atom, or when n is 2, X may also represent a direct bond or a group of the formula (a)

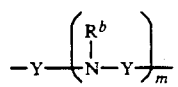

in which $R^b$ represents a hydrogen atom or a group of the following formula

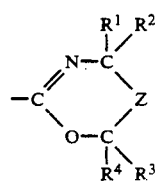

$R^a$'s are identical or different and each represents a hydrogen atom or a monovalent hydrocarbon group which may be interrupted by a hetero atom, $R^1$, $R^2$, $R^3$ and $R^4$ are identical or different and each represents a hydrogen atom, an alkyl group having 1 to 3 carbon atoms, a benzyl group, a phenyl group or a tolyl group, Z is a direct bond or a group of the formula

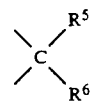

Y is a divalent hydrocarbon group which may be interrupted by a hetero atom, m is an integer of 1 to 10, with the proviso that when m is an integer of 2 to 10, two or more $R^b$'s may be the same or different and $R^5$ and $R^6$ are identical or different and each represents a group selected from the groups defined by $R^1$.

In formula (I), n is an integer of 2 to 10, preferably 2 to 5. X is an n-valent hydrocarbon group which may be interrupted by a hetero atom. Examples of the hydrocarbon group may preferably be aliphatic, alicyclic or aromatic hydrocarbon groups.

X and n are in such a relationship that the valence of the hydrocarbon group X varies with varying n, for example when n is 2, X is a divalent hydrocarbon group and when n is 3, X is a trivalent hydrocarbon group.

Specific examples of the hydrocarbon group X in the case of n being 2 include alkylene groups having 1 to 15 carbon atoms, such as methylene, ethylene, trimethylene, alpha-methylethylene, tetramethylene, pentamethylene, alpha-methyltetramethylene, hexamethylene, trimethylhexamethylene, heptamethylene, 2,2-dimethylpentamethylene, octamethylene, nonamethylene, decamethylene, undecamethylene, dodecamethylene, tridecamethylene, tetradecamethylene and neopentylene; alkylene groups interrupted by an oxygen atom represented by the following formula

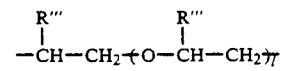

wherein R''' represents hydrogen or a monovalent lower alkyl group such as methyl or ethyl, and l is a number of 15 or below; alicyclic hydrocarbon groups having 6 to 15 carbon atoms such as 1,3-cyclohexylene, 4-methyl-1,3-cyclohexylene,

—[H]—CH$_2$—[H]—,

—[H]—CH(CH$_3$)—[H]—,

—[H]—C(CH$_3$)$_2$—[H]—, (trimethylcyclohexyl group with CH$_3$, CH$_2$—, CH$_3$, CH$_3$) and

—CH$_2$—[H]—CH$_2$—;

monocyclic or bicyclic aromatic hydrocarbon groups having 6 to 15 carbon atoms such as 1,3-phenylene, 1,4-phenylene, 2,4-tolylene, 2,6-tolylene, 2,4- and 2,6-tolylene mixture, p-xylylene, m-xylylene, diethyltoluyl,

—⌬—CH$_2$—⌬—,

—⌬—CH$_2$—,

—⌬—CH$_2$CH$_2$—⌬—, (naphthylene groups);

and monocyclic or bicyclic aromatic hydrocarbon groups interrupted by a hetero atoms such as

—⌬—SO$_2$—⌬—,

—continued

—⌬—O—⌬—,

—⌬—C(O)(O)—C—C(O)(O)—⌬— and

—⌬—CO—⌬—.

When n is 3, examples of X can be $$(CH_2)_n^{|}CH-CO_2-(-CH_2)_{\overline{2}} \quad \text{or}$$

(isocyanurate ring with three tolyl-CH$_3$ N-substituents)

Those skilled in the art would be able to easily understand specific examples of X in the case of n being 4 or more from the specific examples given above for n=2 and n=3.

For example, groups represented by

—⌬—CH$_2$—(⌬—CH$_2$—)$_j$—⌬— wherein j is a number of 1 to 8, may be cited.

When n is 2 in formula (I), X may further be a direct bond or a group of the following formula (a)

$$-Y-\left(\begin{array}{c}R^b\\|\\N-Y\end{array}\right)_m \quad (a)$$

in which R$^b$ represents a hydrogen atom or a group of the following formula $$\begin{array}{c}R^1\ R^2\\|\ |\\-C\diagup N-C\diagdown\\\ \ \ \ \ \ \ \ \ \ \ \ Z\\-C\diagdown O-C\diagup\\|\ |\\R^4\ R^3\end{array}$$

Y is a divalent hydrocarbon group which may be interrupted by a hetero atom, and m is an integer of 1 to 10, with the proviso that when m is an integer of 2 to 10, two or more $R^b$'s may be the same or different.

Examples of the divalent hydrocarbon group Y which may be interrupted by a hetero atom may be those given above with regard to X (n=2).

The symbol m represents an integer of 1 to 10, preferably 1 to 7.

In the above formula, $R^1$, $R^2$, $R^3$ and $R^4$ are identical or different, and each represents hydrogen, alkyl having 1 to 3 carbon atoms, benzyl, phenyl or tolyl. The alkyl having 1 to 3 carbon atoms are methyl, ethyl, n-propyl and iso-propyl.

Preferred X groups in formula (I) are methylene, ethylene, trimethylene, tetramethylene, hexamethylene, 2,2-dimethylpentamethylene, cyclohexylene, 4-methyl-1,3-cyclohexylene,

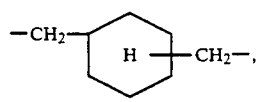

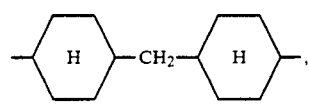

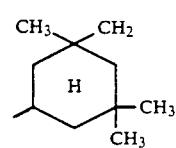

2,4-tolylene, 2,6-tolylene, a 2,4- and 2,6-tolylene mixture, m-xylylene, p-xylylene,

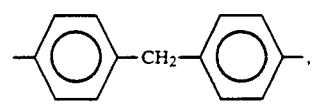

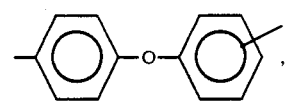

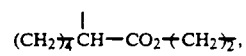

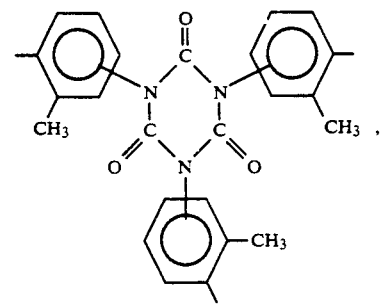

-continued

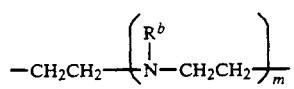

wherein $R^b$ and m are as defined, and

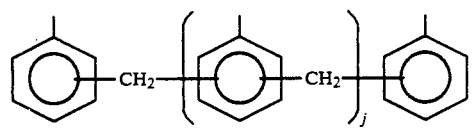

wherein j is a number of 1 to 8.

In formula (I), $R^a$'s are identical or different and each represents a hydrogen atom or a monovalent hydrocarbon group which may be interrupted by a hetero atom. The monovalent hydrocarbon group may be, for example, an aliphatic, alicyclic or aromatic hydrocarbon group. Especially preferred are aliphatic groups having 1 to 8 carbon atoms which may be interrupted by a hetero atom, such as methyl, ethyl, n-propyl, isopropyl, 2-hydroxyethyl, 2-hydroxypropyl and 3-butoxy-2-hydroxypropyl.

Z in formula (I) is a direct bond or a group of the following formula

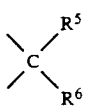

When Z is a direct bond, formula (I) may be written as formula (I)-A below.

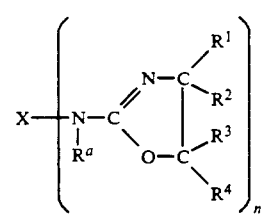

(I)-A wherein X, $R^a$, $R^1$, $R^2$, $R^3$, $R^4$ and n are as defined hereinabove. When Z is the group

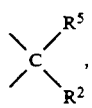

it is represented by the following formula (I)-B.

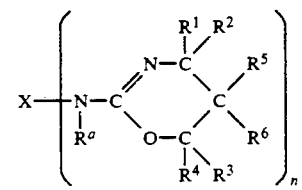

(I)-B

In formulae (I) and (I)-B, $R^5$ and $R^6$ are identical or different, and each represents hydrogen, alkyl having 1 to 3 carbon atoms, benzyl, phenyl or tolyl.

Those skilled in the art would be able to easily understand specific examples of formula (I) from the specific examples of these symbols in formula (I) and the Examples to be given below.

According to this invention, the compound of formula (I) in accordance with this invention can be produced by first (a) reacting a polyisocyanate with a halogenated amine or (b) reacting a polyamine with a halogenated isocyanate to form a polyurea compound, and then in either case, cyclizing the resulting polyurea compound.

The process involving step (a) above will first be described.

This process comprises (1) reacting a polyisocyanate compound represented by the following formula

wherein $X^1$ represents an n-valent hydrocarbon group which may be interrupted by a hetero atom, and n is an integer of 2 to 10, with a haloalkylamine represented by the following formula

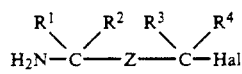

wherein Z is a direct bond or a group of the following formula

in which $R^1$, $R^2$, $R^3$, $R^4$, $R^5$ and $R^6$ are identical or different and each represents hydrogen, alkyl having 1 to 3 carbon atoms, benzyl, phenyl or tolyl, and Hal represents a halogen atom.

(2) then cyclizing the resulting polyurea compound to give a poly(N-cyclic iminoether) compound represented by the following formula (I)-a

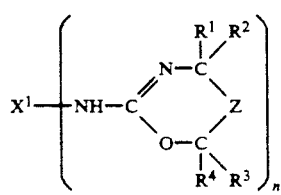

wherein $X^1$, $R^1$, $R^2$, $R^3$, $R^4$, Z and n are as defined above.

In the above formula representing the polyisocyanate compound, $X^1$ represents an n-valent hydrocarbon group which may be interrupted by a hetero atom, and n is an integer of 2 to 10. Specific examples of the hydrocarbon group $X^1$ may be the same as those of the hydrocarbon group X.

The polyisocyanate compound of the above formula may include aliphatic, alicyclic and aromatic polyisocyanates.

Preferred as the aliphatic isocyanates are polyisocyanates such as aliphatic diisocyanates of the following general formula (II) having 3 to 17 carbon atoms

and triisocyanates of the following formula (III)

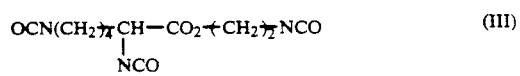

In general formula (II), W is an alkylene group having 1 to 15 carbon atoms, and examples include methylene, ethylene, trimethylene, alpha-methylethylene, tetramethylene, pentamethylene, alpha-methyltetramethylene, hexamethylene, heptamethylene, 2,2-dimethylpentamethylene, octamethylene, nonamethylene, decamethylene, undecamethylene, dodecamethylene, tridecamethylene, tetradecamethylene and pentadecamethylene.

Of these compounds, diisocyanates of general formula (II) in which W is methylene, ethylene, hexamethylene or 2,2-dimethylpentamethylene, and the triisocyanates of the formula

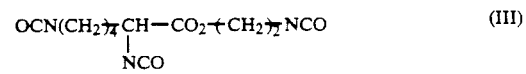

are especially preferred.

Alicyclic diisocyanates having 8 to 17 carbon atoms are preferred as the alicyclic isocyanates. Examples of these diisocyanates include 1,3-diisocyanatecyclohexane, 1,3-diisocyanate-4-methylcyclohexane, 1,3-bis(isocyanatemethyl)cyclohexane, 1,4-bis(isocyanatemethyl)cyclohexane, bis(4-isocyanatecyclohexyl)methane, 1,1-bis(4-isocyanatecyclohexyl)ethane, 2,2-bis(4-isocyanatecyclohexyl)propane and isophorone diisocyanate.

Of these, 1,3-diisocyanatecyclohexane, 1,3-diisocyanate-4-methylcyclohexane, 1,3-bis(isocyanatemethyl)cyclohexane, bis(4-isocyanatecyclohexyl)methane and isophorone diisocyanate are especially preferred.

The aromatic isocyanates may preferably be monocyclic or bicyclic aromatic diisocyanates having 8 to 17 carbon atoms and polycyclic aromatic polyisocyanates of 3 or more rings having about 23 to about 80 carbon atoms. Examples include 1,3-phenylene diisocyanate, 2,4-tolylene diisocyanate, 2,6-tolylene diisocyanate, 2,4- and 2,6-tolylene diisocyanate mixture, xylylene diisocyanate, bis(isocyanatephenyl)methane, bis(isocyanatephenyl)ether, bis(isocyanatephenyl)sulfone, 1-isocyanate-4-isocyanatemethylbenzene, tolylene diisocyanate trimer,

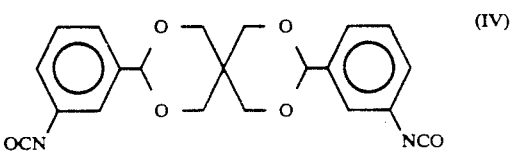

and polyisocyanates represented by the following formula (V)

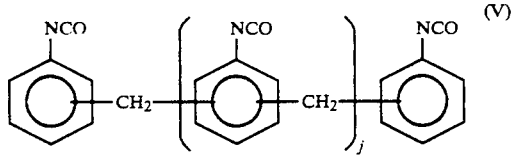 (V)

wherein j is an integer of 1 to 8.

Especially preferred among them are 2,4-tolylene diisocyanate, 2,6-tolylene diisocyanate, 2,4- and 2,6-tolylene diisocyanate mixture, m-xylylene diisocyanate, bis(isocyanatephenyl)methane, tolylene diisocyanate trimer, and the polyisocyanates of formula (V).

The haloalkylamine used in the above process is represented by the following formula

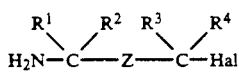

wherein $R^1$, $R^2$, $R^3$, $R^4$ and Z are as defined in formula (I), and Hal is a halogen atom. Chloro, bromo and iodo are preferred as the halogen atom.

Examples of the alkylamine are 2-chloroethylamine, 3-chloropropylamine, 2-chloropropylamine, 2-chloroisobutylamine, 2-amino-1-chloropropane, 2-amino-1-chloroisobutane, 2-amino-3-chlorobutane, 3-chlorobutylamine, 3-chloro-3-methylbutylamine, 3-chloroisobutylamine, 2-amino-4-chlorobutane, 2-amino-4-chloro-2-methylbutane, 2-bromoethylamine, 3-bromopropylamine, 2-iodoethylamine and 3-iodopropylamine. Of these, 2-chloroethylamine and 3-chloropropylamine are preferred.

The reaction of the polyisocyanate compound and the haloalkylamine is carried out preferably in an inert solvent. Desirably, the haloalkylamine is used in the reaction by adding its hydrochloride to a reaction solvent and maintaining it in a free condition with an alkali.

In the reaction, the haloalkylamine is used in a proportion of preferably 0.7 to 5 moles, more preferably 0.8 to 3 moles, especially preferably 0.9 to 1.5 moles.

Desirably, the reaction is carried out at a temperature of $-20°$ to $+150°$ C., preferably $-10°$ to $+120°$ C., especially preferably $-5°$ to $+100°$ C.

The reaction can be carried out under atmospheric pressure or an elevated pressure.

Suitable reaction solvents include amides such as N,N-dimethylformamide and N,N-dimethylacetamide; ethers such as diethyl ether, tetrahydrofuran and dioxane; alcohols such as methanol, ethanol and propanol, halogenated hydrocarbons such as methylene chloride, chloroform, dichloroethane and dibromoethane, sulfoxides such as dimethyl sulfoxide, pyrrolidones such as N-methylpyrrolidone, and ketones such as acetone and methyl isobutyl ketone. These solvents may be used as a mixture.

The polyurea compound obtained by step (1) is then cyclized. Naturally, the polyurea compound may be isolated from the reaction mixture, and then cyclized. It is also possible to cyclize the reaction mixture obtained in step (1) directly without isolating the polyurea compound.

The cyclization reaction may be achieved by carrying out dehalogenating cyclization in the presence of a solvent.

Various known methods may be used in performing the dehydrohalogenating cyclization. For example, there may be preferably used a method which comprises inducing self-cyclization of the polyurea compound in a solvent to form a poly(N-cyclic iminoether) hydrohalide and then dehydrohalogenating it with an alkali, or a method which comprises directly subjecting the polyurea compound with an alkali treatment to perform dehydrohalogenating cyclization. The solvent used at this time may be properly selected from the group of solvents given hereinabove.

Examples of the alkali which may be used are alkali metals such as sodium and potassium, and hydroxides, alcoholate, and salts thereof. The amount of the alkali used is preferably 0.8 to 5.0 equivalents, more preferably 0.9 to 3.5 equivalents, especially preferably 1.0 to 2.0 equivalents, per equivalent of the halogen in the polyurea compound.

The suitable reaction temperature is 10° to 300° C., preferably 30° to 250° C., more preferably 50° to 200° C. The reaction is carried out under atmospheric pressure to elevated pressure.

The above cyclization reaction can give the poly(N-cyclic iminoether) comound of formula (I)-a. This compound can be advantageously purified by, for example, distillation, recrystallization, sublimation, or re-precipitation.

If the compound does not easily become a solid during the course of purification, it is preferable to re-precipitate the reaction mixture as-obtained by the alkali cyclization reaction using a solvent or solvent mixture selected from the above-mentioned solvents, and as required, distill, re-crystallize or sublime the precipitate.

A solvent for recrystallization may be selected from the above group of solvents according to the desired solubilizability.

The poly(N-cyclic iminoether) compound of formula (I)-a has a secondary amino group (—NH—) as seen from formula (I)-a. As required, the secondary amino group may be converted into a tertiary amino group

by, for example, alkylation, addition-reaction with a cyclooxirane, or Michael addition-reaction with an unsaturated compound having a carbon-carbon double bond.

The alkylation, the addition-reaction with a cyclooxirane and Michael addition-reaction are known per se, and the known reaction conditions for these may also be employed in the above case.

Another process for producing the compound (1) of this invention will be described below.

According to this process, the compound of formula (I) in accordance with this invention can be produced by (1) reacting a polyamine compound represented by the following formula

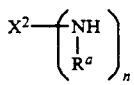

wherein
n is an integer of 2 to 10, $X^2$ is a direct bond or an n-valent hydrocarbon group, or when n is 2, $X^2$ can be a group represented by the following formula (a)′

  (a)′ wherein Y represents a divalent hydrocarbon group which may be interrupted by a hetero atom, and m is an integer of 1 to 10, and $R^a$'s are identical or different and each represents a hydrogen atom or a monovalent hydrocarbon group which may be interrupted by a hetero atom, with a haloalkyl isocyanate represented by the following formula

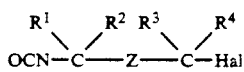

wherein

Z is a direct bond or a group of the formula

$R^1$, $R^2$, $R^3$, $R^4$, $R^5$ and $R^6$ are identical or different and each represents a hydrogen atom, alkyl of 1 to 3 carbon atoms, benzyl, phenyl or tolyl, and Hal represents a halogen atom, (2) thereafter cyclizing the resulting polyurea compound.

In the above formula representing the polyamine compound, $R^a$ and n are as defined in formula (I), and the definition of $X^2$ corresponds to that of X in formula (I).

It is evident from the definitions of the symbols in the above formula that the polyamine compound used in this invention may be an aliphatic, alicyclic or aromatic compound having at least two primary and/or secondary amino groups in the molecule.

Examples of these polyamine compounds include such aliphatic amines as ethylene diamine, trimethylenediamine, tetramethylenediamine, hexamethylenediamine, trimethylhexamethylenediamine, diethylenetriamine, triethylenetetramine, dodecamethylenediamine, neopentylenediamine and polyetherdiamine; such alicyclic polyamines as diaminocyclohexane, 1,3-diamino-4-methylcyclohexane, 1,3-bis-(aminomethyl)cyclohexane, 1,4-bis(aminomethyl)cyclohexane, isophoronediamine, 1,1-bis(4-aminocyclohexyl)ethane, 2,2-bis(4-aminocyclonexyl)propane, bis(4-aminocyclohexyl)methane and bis(aminomethyl)cyclohexane; and such aromatic polyamines as 4,4′-diaminophenylmethane, 4,4′-diaminodiphenylsulfone, 3,3′-diaminodiphenylsulfone, 4,4′-diaminodiphenylether, 3,4′-diaminodiphenylether, 4,4′-diaminobenzophenone, 3,3′-diaminobenzophenone, p-phenylenediamine, m-phenylenediamine, p-xylylenediamine, m-xylylenediamine, diaminonaphthalene, 2,4-diaminotoluene, 2,6-diaminotoluene, 1,2-dianilinoethane, diethyldiaminotoluene, and polyamines represented by the following formula (VI)

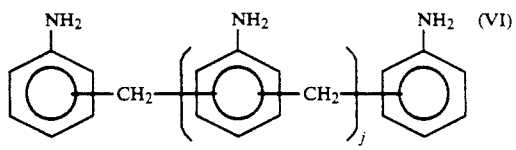

wherein j is an integer of 1 to 8.

Preferred primary amine compounds among them are ethylenediamine, trimethylenediamine, tetramethylenediamine, hexamethylenediamine, diethylenetriamine, triethylenetetramine, diaminocyclohexane, 1,3-bis-(aminomethyl)cyclohexane, 1,3-diamino-4-methylcyclohexane, bis(4-aminocyclohexyl)methane, isophoronediamine, 2,4-diaminotoluene, 2,6-diaminotoluene, m-xylylenediamine, p-xylylenediamine, 4,4′-diaminodiphenylmethane, 4,4′-diaminodiphenylether, 3,4′-diaminodiphenylether, diethyldiaminotoluene and the polyamines of general formula (VI).

Examples of secondary amines are those resulting from substituting an aliphatic, alicyclic or aromatic hydrocarbon group for the hydrogen atom of at least one amino group of the above primary amines. Especially preferably, the above hydrocarbon group is a lower alkyl group such as methyl, ethyl or propyl.

The haloalkyl isocyanate used in the above process is represented by the following formula

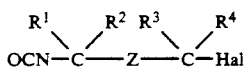

wherein $R^1$, $R^2$, $R^3$, $R^4$ and Z are as defined in formula (I), and Hal is a halogen atom.

$R^1$ to $R^4$, and $R^5$ and $R^6$ in the group

represented by Z are preferably hydrogen or a methyl group. Preferably, Hal is chloro, bromo or iodo.

Examples of the haloalkyl isocyanate include 2-chloroethyl isocyanate, 3-chloropropyl isocyanate, 2-chloropropyl isocyanate, 2-chloroisobutyl isocyanate, 1-chloro-2-isocyanatepropane, 1-chloro-2-isocyanatebutane, 3-chloro-2-isocyanatebutane, 3-chlorobutyl isocyanate, 3-chloro-3-methylbutyl isocyanate, 3-chloroisobutyl isocyanate, 4-chloro-2-isocyanatebutane, 4-chloro-2-isocyanate-2-methylbutane, 2-bromoethyl isocyanate, 3-bromopropyl isocyanate, 2-iodoethyl isocyanate and 3-iodopropyl isocyanate. Preferably used are 2-chloroethyl isocyanate and 3-chloropropyl isocyanate.

The reaction of the polyamine compound with the haloalkyl isocyanate in step (1) is carried out preferably in an inert solvent. The solvent may be the same as those described above with regard to step (1) of the above-described process.

In the reaction, the haloalkyl isocyanate is used in a proportion of 0.7 to 5 moles, preferably 0.8 to 3 moles, especially preferably 0.9 to 1.5 moles, per equivalent of the amino groups of the polyamine. Other reaction conditions in step (1) are the same as the conditions described with regard to step (1) in the above-described process. The reaction conditions for step (2) are also the same as those for step (2) of the process described above.

Thus, according to the alternative process, the poly(N-cyclic iminoether) of formula (I) can be produced.

If a primay amine is used as the polyamine compound in this process, the resulting poly(N-cyclic iminoether) compound has secondary amino groups. These secondary amino groups can also be alkylated by the same method as above.

The poly(N-cyclic iminoether) compound of formula (I) provided by this invention has high reactivity, and therefore can give a thermosetting composition which can be cured at a relatively low curing temperature and/or within a short period of time. The thermosetting composition of this invention containing the poly(N-cyclic iminoether) compound is also characteristic in that it gives a thermoset resin having low molding shrinkage and a high heat distortion temperature.

The thermosetting composition of this invention is provided in some embodiments having novel compositions, namely compositions comprising the poly(N-cyclic iminoether) compound of the invention and (1) a polyepoxy compound, (2) a compound containing at least 2 phenolic hydroxyl groups in the molecule, (3) an ethylenically unsaturated compound having an ethylenically unsaturated bond and a functional group reactive with the poly(N-cyclic iminoether) compound, and (4) a polyisocyanate, respectively.

A first thermosetting composition of this invention comprises (A) the poly(N-cyclic iminoether) compound represented by formula (I), (B) a polyepoxy compound, and (C) optionally a compound selected from the group consisting of compounds having active hydrogen, cyanic acid esters and isocyanates, in such proportions that the amount of the iminoether groups in the poly(N-cyclic iminoether) compound is 0.1 to 10 equivalents per equivalent of the epoxy groups of the polyepoxy compound (B), and the amount of the active hydrogen, cyanate group or isocyanate group of active hydrogen-containing compound, cyanate or isocyanate (C) is not more than 2 equivalents per equivalent of the epoxy groups of the polyepoxy compound (B) and the iminoether groups of the poly(N-cyclic iminoether) compound (A) combined.

The poly(N-cyclic iminoether) compound (A) has been described hereinabove. Part of the poly(N-cyclic iminoether) compound may be replaced by a poly(C-cyclic iminoether) compound (the same can be said with respect to the other compositions to be described below).

The polyepoxy compound (B) used in this invention is a polyepoxy compound containing at least two epoxy groups in the molecule. Examples are given below.

1) Glycidyl ether-type compounds

Aromatic polyols such as 2,2-bis(4-hydroxyphenyl)-propane (bisphenol A), 4,4'-dihydroxydiphenylphenyl) methane, 4,4'-dihydroxydiphenylsulfone, resorcinol, phenol novolak, cresol novolak, resorcinol novolak, naphthol novolak, dihydroxynaphthalene and dihydroxynaphthalene novolak, polyols obtained by the hydration reaction of aromatic hydroxy compounds such as phenol, dihydroxybenzene, naphthol and dihydroxynaphthalene with aldehydes such as glyoxal, glutaraldehyde, p-hydroxybenzaldehyde and benzaldehyde in the presence of an acid catalyst; and glycidyl ethers of polyols, for example polyhydric alcohols such as butanediol, polypropylene glycol, polyethylene glycol and glycerol, and precursor polymers of the glycidyl ethers.

2) Glycidyl ester compounds

Glycidyl esters of dicarboxylic acids such as phthalic acid, isophthalic acid, tetrahydrophthalic acid and naphthalenedicarboxylic acid, and precursor polymers of the glycidyl esters.

3) N-glycidyl type compounds

Compounds obtained by substituting a glycidyl group for the active hydrogen bonded to a nitrogen atom in nitrogen compounds such as aniline, isocyanuric acid and methylenedianiline.

4) Glycidyl ether ester compounds

Glycidyl ether esters of hydroxycarboxylic acids such as p-hydroxybenzoic acid and hydroxynaphthoic acid.

5) Others

Epoxy resins obtained from alicyclic compounds such as cyclopentadiene and dicyclopentadiene, triglycidyl compounds of p-aminophenol and vinylcyclohexene dioxide.

From the viewpoint of availability and the heat resistance of the thermoset resin obtained, preferred are a diglycidyl ether of 2,2'-bis(4-hydroxyphenyl)propane (bisphenol A), a diglycidyl ether of 4,4'-dihydroxydiphenylmethane, a polyglycidyl ether of a phenol novolak, a polyglycidyl ether of naphthol novolak, a polyglycidyl ether of a polyol obtained by dehydration reaction of a phenol with glyoxal, glutaraldehyde, benzaldehyde or p-hydroxybenzaldehyde in the presence of an acid catalyst, a diglycidyl ether of polypropylene glycol, a diglycidyl ether of polyethylene glycol, a diglycidyl ether of butanediol, a diglycidyl ether of glycerol, a triglycidyl ether of glycerol, N,N,N',N'-tetraglycidyl methylenedianiline, a diglycidyl ether ester of p-hydroxybenzoic acid, a diglycidyl ether ester of 2-hydroxy-6-naphthoic acid, a triglycidyl compound of p-aminophenol and vinylcyclohexene dioxide. The glycidyl ether of bisphenol A, the polyglycidyl ether of phenol novolak, the polyglycidyl ether of 2-naphthol novolak and the polyglycidyl ether of the polyol obtained by dehydration reaction of phenol with glyoxal, glutaraldehyde, benzaldehyde or p-hydroxybenzaldehyde in the presence of an acidic catalyst, a diglycidyl ether of polypropylene glycol, a diglycidyl ether of polyethylene glycol, a diglycidyl ether of butanediol, a diglycidyl ether of glycerol, a triglycidyl ether of glycerol, N,N,N',N'-tetraglycidylmethylenedianiline, a triglycidyl compound of p-aminophenol and vinylcyclohexene dioxide are especially preferred. These compounds may be used singly or in combination.

The compound (C) is an optional component, and is a compound having active hydrogen, a cyanate ester, or an isocyanate.

The compound having active hydrogen may preferably be an organic polycarboxylic acid or an intramolecular anhydride thereof, an organic polyhydroxy compound, an organic polyamino compound, an organic hydroxycarboxylic acid, an organic aminocarboxylic acid or an organic hydroxyamino compound which has no ethylenically unsaturated bond and contains at least two equivalents of functional groups of the same or different kinds in the molecule.

Specific examples of the organic polycarboxylic acid include saturated dibasic acids such as phthalic acid, halogenophthalic acid, isophthalic acid, terephthalic acid, hexahydrophthalic acid, methyl hexahydrophthalic acids, dibromotetrahydrophthalic acids, succinic acids, adipic acid, glutaric acid, pimelic acid, azelaic acid, sebacic acid, and dodecanecarboxylic acids, and polybasic acids such as trimellitic acid, hemimellitic acid, trimesic acid and benzenetetracarboxylic acid.

Examples of preferred organic polycarboxylic acids include adipic acid, glutaric acid, azelaic acid, sebacic acid, dodecanedicarboxylic acids, terephthalic acids and isophthalic acids.

Intramolecular anhydrides of the organic polycarboxylic acids having a 1,2- or 1,3-carboxyl group are preferred as the intramolecular acid anhydride of the polycarboxylic acid. Specific examples include aliphatic 1,2- or 1,3-dicarboxylic anhydrides such as succinic anhydride, glutaric anhydrides and methylsuccinic anhydride, alicyclic 1,2-dicarboxylic anhydrides such as cyclohexane-1,2-dicarboxylic anhydrides and 3- or 4-methyl-cyclohexane-1,2-dicarboxylic acids, and aromatic 1,2-dicarboxylic anhydrides such as phthalic anhydride, pyromellitic anhydrides and 3,3',4,4'-benzophenonetetracarboxylic anhydride. Of these, the aliphatic dicarboxylic acid anhydrides such as succinic anhydride and glutaric anhydride, cyclohexane-1,2-dicarboxylic anhydride and phthalic anhydride are preferred.

Specific examples of the polyhydroxy compound include aliphatic hydroxy compounds such as ethylene glycol, propylene glycol, trimethylene glycol, butanediol, hexanediol, octanediol, decamethylene glycol, diethylene glycol, triethylene glycol, glycerol, trimethylolpropane, pentaerythritol, polyoxyethylene glycol, neopentylene glycol, polyoxytetramethylene glycol, bishydroxyethyl terephthalate and bishydroxyethyl isophthalate; alicyclic hydroxy compounds such as cyclohexanedimethanol, dihydroxycyclohexane and trihydroxycyclohexane; aromatic hydroxy compounds such as hydroquinone, resorcinol, methylhydroquinone, chlorohydroquinone, t-butylhydroquinone, t-amylhydroquinone, fluorohydroquinone, bromohydroquinone, 2,5-dichlorohydroquinone, pyrogallol, catechol, 1,3,5-trihydroxybenzene, 2,2-bis(4-hydroxyphenyl)propane, 4,4'-dihydroxydiphenyl, 4,4'-dihydroxydiphenyl ether, 4,4'-dihydroxydiphenylsulfide, 4,4'-dihydroxydiphenylmethane, 1,1-bis(4-hydroxyphenyl)cyclohexane, phenolphthalein, 1,1-bis(4-hydroxyphenyl)ethane, 2,2-bis(3-methyl-4-hydroxyphenyl)propane, 2,2-bis(3,5-dimethyl-4-hydroxyphenyl)propane, 3,4'-dihydroxydiphenyl ether; halogenated bisphenols such as 2,2-bis(3-chloro-4-hydroxyphenyl)propane, 2,2-bis(3,5-dichloro-4-phenyl)propane, 2,2-bis(3-bromo-4-hydroxyphenyl)propane, 2,2-bis(3,5-dibromo-4-hydroxyphenyl)propane, bis(3,5-dichloro-4hydroxyphenyl)methane, 1,1-bis(3,5-dichloro-4-hydroxyphenyl)ethane, 1,1-bis(3,5-dibromo-4-hydroxyphenyl)ethane, bis(3,5-dichloro-4-hydroxyphenyl)sulfone, bis(3,5-dibromo-4-hydroxyphenyl)sulfone, bis(3,5-dichloro-4-hydroxyphenyl)sulfone, 1,1-bis(3,5-dibromo-4-hydroxyphenyl)cyclohexane, 1,1-bis(3,5-dibromo-4-hydroxyphenyl)cyclohexane, bis(3,5-dichloro-4-hydroxyphenyl)ether, bis(3,5-dibromo-4-hydroxyphenyl)ether, bis(3,5-dibromo-4-hydroxyphenyl)sulfide and bis(3,5-dibromo-4-hydroxyphenyl)ketone; and dihydroxynaphthalene; and polyol compounds obtained by a known process comprising dehydrocondensation of phenols and aldehydes in the presence of an acid or alkaline catalyst.

Examples of the phenols used in the production of the polyol compound mentioned above may be aromatic hydroxyl-containing compounds such as phenol, cresol, hydroquinone, resorcinol, xylenol, alpha-naphthol, beta-naphthol and dihydroxynaphthalene. Of these, phenol is preferred. Examples of the aldehyde used in the production of the polyol compounds are formaldehyde, acetaldehyde, glyoxal, glutaraldehyde, benzaldehyde, p-hydroxybenzaldehyde, m-hydroxybenzaldehyde and terephthalaldehyde. Formaldehyde is especially preferred.

Especially preferred polyhydroxy compounds are, for example, aromatic polyhydroxy compounds such as 2,2-bis(4-hydroxyphenyl)propane, 4,4'-dihydroxydiphenylmethane, resorcinol, halogenated bisphenols such as 2,2-bis(3,5-dichloro-4-hydroxyphenyl)propane and 2,2-bis(3,5-dibromo-4-hydroxyphenyl)propane, and polyhydroxy compounds having a phenolic hydroxyl group such as phenol novolak.

The organic polyamino compounds used in this invention may be aliphatic, alicyclic and aromatic compounds having at least two primary and/or secondary amino groups in the molecule. Specific examples include aliphatic polyamine compounds such as ethylenediamine, trimethylenediamine, tetramethylenediamine, hexamethylenediamine, trimethyl hexamethylenediamine, diethylenetriamine, triethylenetetramine, tetraethylene pentamine, dodecamethylenediamine, neopentylenediamine, and dicyandiamide; alicyclic polyamine compounds such as diaminocyclohexane, isophoronediamine, piperadine, 1-(2-aminoethyl)piperadine, bis(4-aminocyclohexyl)methane, bis(aminomethyl)cyclohexane and 1,8-p-menthanediamine; aromatic polyamine compounds such as 4,4'-diaminodiphenylmethane, 4,4'-diaminodiphenylsulfone, 3,3'-diaminodiphenylsulfone, 4,4'-diaminodiphenylether, 3,4'-diaminodiphenylether, 4,4'-diaminobenzophenone, 3,3'-diaminobenzophenone, p-phenylenediamine, m-phenylenediamine, p-xylylenediamine, m-xylylenediamine, diaminonaphthalene, 4,4'-diaminodiphenylsulfide, 2,4-diaminotoluene, 2,6-diaminotoluene, 1,2-dianilinoethane, diethyldiaminotoluene, and eutectic mixtures of these.

Preferred among them are diethylenetriamine, triethylenetetramine, tetraethylenepentamine, 1,8-p-menthanediamine, hexamethylenediamine, dicyandiamide, 1-(2-aminoethyl)piperazine, m-xylylenediamine, metaphenylenediamine, 4,4'-diaminodipenylmethane, 3,3'- and 4,4'-diaminodiphenylsulfone,2,4-tolylenediamine and bis(4-aminocyclohexyl)methane.

The organic isocyanates that can be used may be the same as the polyisocyanate compounds used as starting materials in the production of the poly(N-cyclic iminoether) compounds of the invention.

Examples of the organic cyanate compound are phenylene dicyanate, 2,2-bis(4-cyanatephenyl)propane, 4,4'-dicyanatediphenyl, 4,4'-dicyanatediphenyl ether and polycyanates of the following formula (VIII).

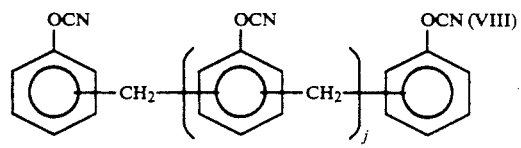

wherein j is an integer of 1 to 8. Of these, 2,2-bis(4-cyanatephenyl)propane and the polycyanates of the formula (VIII) are especially preferred.

The compounds containing dissimilar functional groups may include, for example, organic hydroxycarboxylic acids such as p-hydroxybenzoic acid and salicyclic acid; organic aminocarboxylic acids such as p-aminobenzoic acid or DL-alanine; organic hydroxyamino compounds such as aminophenol and ethanolamine; carboxylic acid anhydrides such as trimellitic anhydride. Of these organic hydroxycarboxylic acids such as p-hydroxybenzoic acid and salicylic acids, trimellitic anhydride and aminophenol are preferred.

As the component (C), one or a combination of two or more of the above compounds may be used.

In the first thermosetting composition, the poly(N-cyclic iminoether) compound (A) and the polyepoxy compound (B) are used in such proportions that the amount of the iminoether groups of the poly(N-cyclic iminoether) compound (A) is 0.1 to 10 equivalents, preferably 0.15 to 7 equivalents, more preferably 0.2 to 5 equivalents per equivalent of the epoxy groups of the polyepoxy compound (B).

The optional compound (C) is used in such a proportion that the amount of the active hydrogen, cyanate group or isocyanate group is not more than 2 equivalents, preferably not more than 1.8 equivalents, more preferably 1.6 equivalents per equivalent of the iminoether groups of compound (A) and the epoxy groups of the compound (B) combined.

If the proportions of the components are outside the above-mentioned ranges, the reactivity of the composition tends to decrease. The unreacted compound (B) and the unreacted comound (C) may remain in the thermoset resin, and various properties of the produt tends to be degraded.

The first thermosetting composition changes to a cured resin under heat. The curing reaction proceeds at room temperature or at an elevated temperature, and the reaction time becomes shorter as the temperature becomes higher.

The reaction temperature, which varies depending upon the types of the compounds (A), (B) and (C) and the type of the reaction that takes place, is usually 50° to 350° C., preferably 65° to 300° C., more preferably 80° to 250° C. The reaction time is about 10 seconds to 10 hours, preferably 20 seconds to 5 hours, more preferably 30 seconds to 2 hours.

The curing reaction is an exothermic reaction, and therefore, may be carried out while removing the heat of reaction.

Preferably, the above reaction is carried out in a mold, and it is desirable to obtain a cured resin (molded article) by the so-called reactive molding technique. For example, there may be employed a one-package method which comprises mixing the above ingredients by dry blending, slurry blending or melt blending, pouring the blended mixture into a mold, and reacting them under heat, or a two-package method which comprises melting the above ingredients individually in separate systems, or melting two or more mixtures of these ingredients in arbitrary proportion, directly pouring the molten masses into a mold maintained, controlled, at or to a predetermined temperature by using a mixing head or the like, and reacting the mixture.

In the present invention, the above reaction may be carried out by using a reaction catalyst. The use of the catalyst is preferred in order to promote or control the reaction. The catalyst may be, for example, a catalyst for ring-opening reaction of the cyclic iminoether groups of component (A), a catalyst for ring-opening reaction of the epoxy groups of component (B), or a catalyst for reacting the amino group with the epoxy groups when component (A) has the amino group [when $R^a$ in formula (I) is a hydrogen atom].

Specific examples of such catalysts are shown below.
(1) Protonic acids having a pKa of not more than 2.5.
(2) Esters of protonic acids having a pKa of not more than 1.0,
(3) Salts of protonic acids having a pKa of not more than 2.5,
(4) Lewis acids and complexes thereof,
(5) Alkyl halides,
(6) Iodine,
(7) Halogenophenols in which the benzene ring is substituted by a halogen atom and an electron attracting group,
(8) Halogenophthalic acids in which the benzene ring is substituted by a halogen atom, and derivatives thereof including their acid anhydride,
(9) Secondary or tertiary amines or salts thereof,
(10) Phenols,
(11) Mercaptans,
(12) Imidazoles,
(13) Lithium compounds, and
(14) Alkoxides and phenoxides of metals of Groups IIA and IIIB of the periodic table.

The compounds (1) to (8) are disclosed in European Patent Application No. 273368 laid open on Jul. 6, 1988. The description of these compounds (1) to (8) in European Patent Application No. 273368 is cited herein as the disclosure of compounds (1) to (8) in this specification.

Examples of the secondary or tertiary amines or their salts (9) include triethylamine, N,N-dimethylcyclohexylamine, N,N,N',N'-tetramethyldiamine, N,N,N',N'-tetramethylpropane-1,3-diamine, N-methylmorpholine, dimethylaminoethanol, N-methyl-N'-(2-hydroxyethyl)-piperazine, bis(2-dimethylaminoethyl)ether, tri(dimethylaminomethyl)phenol, N-methylpiperazine, hydroxyethylpiperazine, piperidine, pyrrolidine, morpholine, N,N'-dimethylpiperazine, hexamethylenetetramine, triethylenediamine, pyridine, pyrazine, quinoline, benzyldimethylamine, alpha-methylbenzyldimethylamine, 2,4,6-tris(dimethylaminomethyl)phenol, 1-pantachlorophenyldiethylenetriamine, N,N'-(hexachlorobiphenylene)bis(ethylenediamine), 1,1'-(hexachlorobiphenylene)bis(diethylenetriamine) and hydrochlorides and tri-2-ethylhexanoates of these.

Examples of the phenols (10) are phenol, pentachlorophenol, and the poly(aromatic alcohols) described as component (C) of the first thermsetting composition of this invention.

Examples of the mercaptans (11) are mercaptan, polymercaptan, trimercaptomethyl trioxane, and polysulfide resins having a mercaptan group at both ends.

One example of the imidazole (12) is 2-ethyl-4-methylimidazole.

Examples of the lithium compounds (13) are lithium butoxide and lithium chloride.

Examples of the alkoxides and phenoxides of metals of Groups IIA and IIIB of the periodic table (14) are aluminum isopropoxide, aluminum phenoxide, potassium ethoxide and magnesium ethoxide.

Tin octylate, 2-(2-dimethylaminoethoxy)-4-methyl-1,3,2-dioxabornane, tris(alkylamino)silanes, diacetoacrylamide/amine complex, and siloxanes having an amine functional group may also be used as the catalyst.

The reaction catalyst is used in an amount of preferably 0.01 to 20 mole %, more preferably 0.02 to 10 mole %, especially preferably 0.03 to 5 mole %, based on the total amount in moles of the components (A), (B) and (C).

A second thermosetting composition of this invention comprises (A) a poly(N-cyclic iminoether) represented by formula (I), and (B) a compound having at least 2 phenolic hydroxyl groups in the molecule, in such proportions that the amount of the phenolic hydroxyl groups of the compound (B) is 0.3 to 1.5 equivalents per equivalent of the iminoether groups of the compound (A).

The poly(N-cyclic iminoether) compound (A) is as described hereinabove.

Examples of the compound (B) having at least 2 phenolic hydroxyl groups are the same aromatic hydroxy compounds as described above as component (C) of the first thermosetting composition, 2,2-bis(3-allyl-4-hydroxyphenyl)propane, 2-(3-allyl-4-hydroxyphenyl)-2-(4-hydroxyphenyl)propane, bis(3-allyl-4-hydroxyphenyl)methane, and 3-allyl-4-hydroxyphenyl-p-hydroxytoluene. Of these, 2,2-bis(4-hydroxyphenyl)propane, 4,4'-dihydroxydiphenylmethane, resorcinol and a polyol compound obtained by dehydrocondensation of phenol and formaldehyde are preferred.

In the second thermosetting composition, components (A) and (B) are used in such proportions that the amount of the phenolic hydroxyl groups of component (B) is 0.3 to 1.5 equivalents, preferably 0.4 to 1.4 equivalents, more preferably 0.5 to 1.3 equivalents, per equivalent of the iminoether groups of component (A).

The curing reaction is carried out at a temperature of preferably 50° to 300° C., more preferably 60° to 280° C., especially preferably 70° to 260° C. The reaction time is preferably 10 seconds to 120 minutes, more preferably 20 seconds to 100 minutes, especially preferably 30 seconds to 80 minutes.

The curing reaction may be carried out in a mold as in the case of the first thermosetting composition by a one-package or two-package method. When it is performed by the two-package method, it is preferred to provide one package composed mainly of the component (A) and another package composed mainly of component (B) and optionally a catalyst.

Compounds (1) to (8) described for the first thermosetting composition may be favorably used as the catalyst for the second thermosetting composition.

These catalysts may be used singly or in combination in an amount of 0.01 to 20 mole %, preferably 0.05 to 14 mole %, especially preferably 0.1 to 10 mole %, per equivalent of the iminoether groups of component (A).

A third thermosetting composition of this invention comprises (A) a poly(N-cyclic iminoether) compound of formula (I), (B) an ethylenically unsaturated compound having an ethylenically unsaturated bond and a functional group capable of reacting with the cyclic iminoether groups of the poly(N-cyclic iminoether) compound, and (C) optionally, an ethylenically unsaturated monomer having an ethylenically unsaturated bond but having no functional group capable of reacting with the cyclic iminoether groups of the poly(N-cyclic iminoether) compound, in such proportions that 2 to 150 parts by weight of the poly(N-cyclic iminoether) compound and 0 to 200 parts by weight of the ethylenically unsaturated monomer (C) are used per 100 parts by weight of the ethylenically unsaturated compound (B).

The compound (A) has already been described above.

The component (B) used in this invention is an ethylenically unsaturated compound having in the molecule at least one functional group reactive with the cyclic iminoether group of the poly(N-cyclic iminoether) (A) and at least one ethylenically unsaturated bond.

The functional group capable of reacting with the cyclic iminoether groups is preferably a carboxyl group, a hydroxyl group, an amino group, an epoxy group, or an intramolecular carboxylic acid anhydride group.

Both high molecular compounds and low molecular compounds may be used as the component (B). Examples of preferred compounds (B) may include high molecular compounds such as unsaturated polyesters having carboxyl or hydroxyl groups, and low molecular compounds such as organic polycarboxylic acids, intramolecular acid anhydrides, organic polyhydroxy compounds, organic polyamino compounds and organic polyepoxy compounds which have an ethylenically unsaturated bond.

A carbon-carbon double bond adjacent to the carbonyl group, for example, is preferred as the ethylenically unsaturated bond of the component (B).

The unsaturated polyesters as component (B) are preferably unsaturated polyesters having a molecular weight of about 500 to 10,000 produced by a known method from alpha,beta-unsaturated dibasic acids and/or their ester-forming derivatives with or without saturated dibasic acids and/or their ester-forming derivatives as a dibasic acid component and polyhydric alcohols and/or organic epoxides such as propylene oxide as an alcohol component.

Examples of the alpha,beta-unsaturated dibasic acids include maleic acid, halogenated maleic acid, fumaric acid, citraconic acid, itaconic acid, halogenated itaconic acid, 5-norbornene-2,3-dicarboxylic acid, methyl-5-norbornene-2,3-dicarboxylic acid, tetrahydrophthalic acid, methyltetrahydrophthalic acid, intramolecular acid anhydrides of these acids, and alkyl esters of these acids. Examples of the saturated dibasic acids are phthalic acid, halogenated phthalic acid, phthalic anhydride, halogenated phthalic anhydride, isophthalic acid, terephthalic acid, hexahydrophthalic acid, hexahydrophthalic anhydride, methylhexahydrophthalic acid, methylhexahydrophthalic anhydride, dibromotetrahydrophthalic acid, dibromotetrahydrophthalic anhydride, succinic acid, succinic anhydride, adipic acid, glutaric acid, pimelic acid, azelaic acid, sebacic acid, and alkyl esters of these acids. As required, monobasic acids such as acrylic acid, methacrylic acid, propionic acid, butyric acid, valeric acid, higher fatty acids, benzoic acid, p-hydroxybenzoic acid and octylic acid and polybasic acids such as trimellitic acid, hemimellitic acid, trimesic acid and benzenetetracarboxylic acid may be used as a modifier.

Examples of the polyhydric alcohol include ethylene glycol, diethylene glycol, triethylene glycol, polyethylene glycol, propylene glycol, dipropylene glycol, tripropylene glycol, polypropylene glycol, 1,3- or 1,4-butylene glycol, tetramethylene glycol, 1,6-hexanediol, neopentyl glycol, hydrogenated bisphenol A, bisphenol A ethylene oxide, and/or propylene oxide adduct.

The polyhydric alcohol is used in an amount substantially equivalent to the dibasic acid component, or in excess of the latter by not more than 20 mole %. As required, monohydric alcohols such as amyl alcohol, hexyl alcohol, pentyl alcohol, octyl alcohol, nonyl alcohol, decyl alcohol and tetrahydrofurfuryl alcohol, and polyhydric alcohols such as glycerol, pentaerythritol, trimethylolethane, trimethylolpropane, trimethylolbutane, sorbitol, erythritol and mesoerythritol may be used as a modifier.

Examples of the organic epoxides include alkylene oxides such as ethylene oxide, 1,2-propylene oxide and epichlorohydrin; glycidyl ethers such as methyl glycidyl ether, ethyl glycidyl ether and allyl glycidyl ether, and glycidyl esters such as methyl glycidyl ester, ethyl glycidyl ester and allyl glycidyl ester. These polyepoxides are used in an amount substantially equivalent to the dibasic acid component or in excess of the latter by not more than 20 mole %.

The unsaturated polyesters may be used as a mixture with each other or with a low molecular compound.

Examples of the organic polycarboxylic acids or their intramolecular anhydrides as component (B) include maleic acid, halogenated maleic acid, fumaric acid, citraconic acid, itaconic acid, halogenated itaconic acid, 5-norbornene-2,3-dicarboxylic acid, methyl-5-norbornene-2,3-dicarboxylic acid, tetrahydrophthalic acid, methyltetrahydrophthalic acid, tetrachlorophthalic acid and intramolecular acid anhydrides of these acids.

Examples of the organic polyhydroxy compounds include aliphatic hydroxy compounds such as 2-butene-1,4-diol such as 2-hydroxyethyl fumarate, and aromatic hydroxy compounds such as 3,3'-diallyl bisphenol A, allyl bisphenol A, bis(3-allyl-4-hydroxyphenyl)methane and 3-allyl-4-hydroxyphenyl-p-hydroxytoluene.

Preferably, the organic polyamino compounds may be, for example, aromatic amines and amines having a methylamino group bonded to an aromatic ring, typically 2,4-diaminostyrene.

Examples of the organic polyepoxy compound include glcidyl esters of carboxylic acids containing an ethylenically unsaturated bond as described above, and glycidyl ethers of hydroxy compounds containing an ethylenically unsaturated bond, specifically diglycidyl fumarate, diglycidyl maleate, and diglycidyl ether of 3,3'-diallyl bisphenol A.

Compounds having only one functional groups reactive with the iminoether group in the molecule such as 2-hydroxyethyl methacrylate, 2-hydroxyethyl acrylate and 2-aminoethyl methacrylamide and glycidyl methacrylate may also be used as the component (B).

The aforesaid low molecular compounds may be used singly or in combination with each other.

As component (B), the low-molecular compounds and the unsaturated polyesters may each be used as a mixture of two or more.

The unsaturated polyesters, maleic anhydride and itaconic acid are especially preferably used as component (B) in the third thermosetting composition of this invention.

The component (C) optionally used in this invention is an ethylenically unsaturated monomer having an ethylenically unsaturated bond but no functional group capable of reacting with the cyclic iminoether group of the poly(N-cyclic iminoether).

Preferred examples of the component (C) are styrenes represented by the following formula

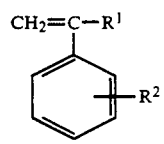

wherein $R^1$ represents a hydrogen atom or a methyl group, $R^2$ represents a hydrogen atom, an alkyl group having 1 to 4 carbon atoms, a halogen atom or a group of the formula

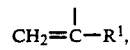

(meth)acrylates represented by the following formula

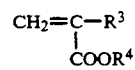

wherein $R^3$ represents a hydrogen atom or a methyl group, and $R^4$ represents an alkyl group having 1 to 10 carbon atoms or a tetrahydrofurfuryl group, vinyl acetate, allyl esters of aromatic polycarboxylic acids, and triallyl (iso)cyanurate.

Examples of the styrenes of the above formula are styrene, alpha-methylstyrene, t-butylstyrene, chlorostyrene, vinyltoluene and divinylbenzene.

Examples of the (meth)acrylates are esters of acrylic or methacrylic acid with aliphatic alcohols such as methanol, ethanol, propanol, octanol, hexanol and tetrahydrofurfuryl alcohol.

Examples of the allyl esters of aromatic polycarboxylic acids are diallyl phthalate and diallyl isophthalate.

The compounds as the component (C) may be used singly or in combination. Styrene is especially preferred as the component (C).

In the third thermosetting composition, component (A) is used in an amount of 2 to 150 parts by weight, preferably 3 to 140 parts by weight, more preferably 5 to 130 parts by weight, per 100 parts by weight of component (B).

The amount of the optional component (C) is not more than 200 parts by weight, preferably not more than 180 parts by weight, more preferably not more than 150 parts by weight, per 100 parts of component (A).

The third thermosetting composition may also include the polyepoxy compound, the compound having active hydrogen, the cyanate ester or the isocyanate constituting the first thermosetting resin composition. Of the organic polyamino compounds, aromatic polyamine compounds are particularly preferred. If compounds (B) and (D) contain epoxy groups, aliphatic and alicyclic polyamines may also be used preferably. The amount of this compound is preferably not more than 150 parts by weight, more preferably 120 parts by weight, especially preferably not more than 100 parts by weight, per 100 parts by weight of components (A) and (B) combined.

The third thermosetting composition may be subjected to a curing reaction at a temperature of preferably 35° to 280° C., more preferably 45° to 240° C., especially preferably 55° to 220° C. The reaction time is preferably 10 seconds to 90 minutes, more preferably 20 seconds to 60 minutes, especially preferably 30 seconds to 45 minutes.

In the curing reaction of the third thermosetting composition, the compounds (1) to (8) described as the catalyst for the first thermosetting composition may be used as cationic catalysts. If the third thermosetting composition contains the polyepoxy compound, the active hydrogen-containing compound, the cyanate ester or the isocyanate, the use of the compounds (9) to (14) described above for the first thermosetting composition as catalysts is desirable for promoting the curing reaction.

These catalysts may be used singly or in combination.

The catalysts (1) to (14) are used in an amount of preferably 0.01 to 20 mole %, more preferably 0.05 to 15 mole %, especially preferably 0.1 to 10 mole %, per equivalent of the cyclic iminoether groups of the component (A).

The third thermosetting composition of this invention contains compounds having an ethylenically unsaturated bond as components (B) and (C). To promote polymerization or crosslinking reaction owing to the cleavage of the ethylenically unsaturated bond, the third thermosetting composition may contain a radical catalyst.

An organic peroxide is preferably used as the radical catalyst used in this invention. Specific examples of the organic peroxide include ketone peroxides such as methyl ethyl ketone peroxide, cyclohexanone peroxide and methyl isobutyl ketone peroxide; hydroperoxides such as cumene hydroperoxide and tertiary butyl hydroperoxide; peroxy esters such as t-butyl peroxyoctoate and t-butyl peroxybenzoate; dialkyl peroxides such as 1,3-bis(t-butyl peroxyisopropyl)benzene, dicumyl peroxide and tris-(t-butylperoxy)triazine, diacyl peroxides such as isobutyryl peroxide, lauroyl peroxide and benzoyl peroxide; peroxyketals such as 1,1-di-t-butylperoxy-3,3,5-trimethylcyclohexane, 1,1-di-t-butylperoxycyclohexane and 2,2-di(t-butylperoxy)butane; and percarbonates such as t-butylperoxyisopropyl carbonate, bis(4-t-butylcyclohexyl)peroxy dicarbonate and di-3-methoxybutyl peroxydicarbonate.

These radical catalysts may be used singly or in combination. The amount of the radical catalyst used is 0.05 to 15% by weight, preferably 0.1 to 10% by weight, especially preferably about 0.2 to 5% by weight, based on the total weight of the components (B) and (C). As required, a small amount of organic acid salts of polyvalent metal, for example a salt of a heavy metal such as cobalt, manganese, iron or copper with octylic acid or naphthenic acid, and a polymerization promoter, for example a tertiary amines such as dimethylaniline or dimethyl-p-toluidine, and a polymerization inhibitor such as hydroquinone, naphthoquinone, t-butylcatechol, p-benzoquinone, butylated hydroxytoluene and nitroxide radical may preferably be added to the radical catalyst in order to control the reaction rate and improve the pot life of the catalyst.

The curing reaction of the third thermosetting composition may be carried out as in the case of the first composition in a mold by the one-package or two-package method.

The two-package method is preferred. It is especially preferred to use one package composed of the component (A), the optional component (C), another component such as a polyepoxide and the radical catalyst, and another package composed of component (B), the optional component (C) and the cationic catalyst.

According to this invention, there is also provided a process for producing a thermoset resin, which comprises reacting under heat (A) a poly(N-cyclic iminoether) compound of formula (I), (B) a polyisocyanate, (C) a compound having at least two groups selected from alcoholic hydroxyl groups and amino groups, and (D) a compound having at least two phenolic hydroxyl groups in the molecule, said components being used in such proportions that the total amount of the alcoholic hydroxyl and/or amino groups of compound (C) and optionally the secondary amino groups of compound (A) is at least equivalent to the amount of the isocyanate groups of the polyisocyanate (B), the amount of the phenolic hydroxyl groups of compound (D) is up to 2 equivalents to the cyclic iminoether groups of compound (A), and the total amount of components (B) and (C) is 10 to 1000 parts by weight per 100 parts by weight of components (A) and (D) combined.

The components (A) and (B) may be the same as those exemplified above with regard to the first thermosetting composition.

Examples of the compound having in the molecule at least two groups selected from alcoholic hydroxyl and amino groups are organic polyamino compounds, organic polyhydroxyl compounds and organic hydroxyamino compounds.

The organic polyamino compounds and organic hydroxyamino compounds may be the same as those exemplified with regard to the first thermosetting composition. Examples of the organic hydroxyl compounds are the aliphatic or alicyclic hydroxyl compounds exemplified above with regard to the first thermosetting composition.

Additional examples include such amines as 2,4,6-triethyl-m-phenylenediamine, 2,6-dimethyl-4-t-butyl-m-phenylenediamine, 4,6-diisopropyl-m-phenylenediamine, bis(3,5-dimethyl-4-aminophenyl)methane, N,N'-dimethyl-m-phenylenediamine and N,N'-diethyl-m-phenylenediamine.

Preferably, the oligomer or polymer containing at least two hydroxyl and/or amino groups are substantially linear and have a flow initiating temperature of not more than 300° C., particularly not more than 280° C. It is to be understood in this invention that an oligomer or polymer in which at least 50 mole %, preferably at least 60 mole %, more preferably at least 70 mole %, especially preferably at least 80 mole %, on an average, of the entire terminal groups are hydroxyl and/or amino groups have at least two hydroxyl and/or amino groups. Examples of such an oligomer or polymer include polyamides, polyethers, polysulfones, polyurethanes, polyesters, polyetherimides, polyetherketones, polyphenylene sulfides, polyethylene, polyazomethine and polyamideimides. The above oligomer or polymer having hydroxyl and/or amino groups as terminal groups may be produced by methods known per se.

The flow initiation temperature denotes a temperature at which a polymer sample can be melt-extruded by a flow tester equipped with a nozzle having a diameter of 0.5 mm and a length of 1 mm under a pressure of 100 kg/cm$^2$. The above oligomer or polymer may have an inherent viscosity of about 0.05 to 0.7.

In the present invention, the above organic compounds (C) may be used singly or in combination with each other.

The compound (D) having at least two phenolic hydroxyl groups in the molecule may be the same as those exemplified above as component (B) of the second thermosetting composition.

The quantitative relation of the individual components (A), (B), (C) and (D) are as follows:- The proportions of the compounds (A), (B) and (C) are such that the total amount of the alcoholic hydroxyl groups and/or amino groups of compound (C) and sometimes, the secondary amino groups of the compound (A) as well is at least 1 equivalent, preferably 1 to 3 equivalents, especially preferably 1 to 2 equivalents, per equivalent of the isocyanate groups of the polyisocyanate (B). The component (D) is used in such an amount that the amount of the phenolic hydroxyl groups of component (D) is up to 2 equivalents, preferably up to 1.6 equivalents, more preferably up to 1.2 equivalents, per equivalent of the cyclic iminoether groups of component (A). It is also necessary that in the above quantitative relation, the total amount of components (B) and (C) should be 10 to 1,000 parts by weight, preferably 20 to 900 parts by weight, more preferably 20 to 800 parts by weight, per 100 parts by weight of components (A) and (D) combined.

The above reaction under heat is carried out at a temperature of preferably 20° to 250° C., more preferably 25° to 220° C., especially preferably 30° to 200° C. The reaction time is preferably 5 seconds to 90 minutes, more preferably 10 seconds to 60 minutes, especially preferably 30 seconds to 45 minutes.

The curing reaction under heat can be carried out in a mold as is the case with the first thermosetting composition by the one-package or two-package method.

Compounds (1) to (8) (cationic catalysts) described above with regard to the first thermosetting composition may preferably be used as a reaction catalyst.

To promote the reaction of the polyisocyanate (B) with the compound (C) having an alcoholic hydroxyl group, the compounds (9) to (14) described above with regard to the first thermosetting composition, and organometallic catalysts such as stannous octoate, dibutyltin laurate, dibutyltin dimaleate and dioctyltin mercaptide may be used. When the organometallic catalyst is used, the joint use of an amine can further promote the reaction.

The amount of the above catalyst is preferably 0.01 to 10% by weight, more preferably 0.03 to 8% by weight, especially preferably 0.05 to 6% by weight, based on the polyisocyanate (B).

When the curing reaction under heat is carried out by the two-package method, it is preferable to use one package composed of components (A) and (C) and optionally, a reaction promoter catalyst for isocyanates and alcoholic OH and another package composed of components (B) and (D) and the cationic catalyst.

As required, additives may be incorporated in the thermoset resins of this invention. The additives include, for example, reinforcing materials such as aramid fibers, carbon fibers or glass fibers, fillers, pigments, coloring agents, oxidation stabilizers, ultraviolet absorbers, flame retardants and mold releasing agents.

The following examples illustrate the present invention in more detail. It should be understood however that these examples do not in any way limit the scope of the invention described and claimed herein.

In the following examples, all parts are by weight unlesss otherwise specified. The infrared absorption spectrum (IR) was measured by the KBr method. The nuclear magnetic resonance spectrum (NMR) was measured by using $d_6$-dimethyl sulfoxide (d-chloroform in FIG. 18) as a solvent and tetramethylsilane as a standard sample.

The heat distortion temperature (HDT for short) of a molded plate sample was measured at a temperature elevation rate of 10° C./min. by a DMA (device for measuring dynamic thermomechanical properties) after the sample was heat-treated at 150° C. for 5 hours.

EXAMPLE 1A

Synthesis of N,N'-diethyl-N,N'-bis(2-oxazolinyl)ethylenediamine

A solution of 29.1 parts of N,N'-diethylethylenediamine in 80 cc of methylene chloride was added dropwise over 30 minutes to a solution of 52.8 parts of chloroethyl isocyanate in 150 cc of methylene chloride, and the mixture was heated under refluxing for 2 hours. After the reaction, the solid which precipitated was collected by filtration and then dried under reduced pressure to give 75.6 parts of a white solid. The resulting solid (70 parts) was added to a solution of 30.1 parts of potassium hydroxide in 400 cc of methanol and reacted under refluxing for 5 hours. The reaction mixture was hot-filtered, concentrated under reduced pressure, and distilled under reduced pressure to give 12.2 parts of N,N'-diethyl-N,N'-(2-oxazolinyl)ethylenediamine.

Figure 2:
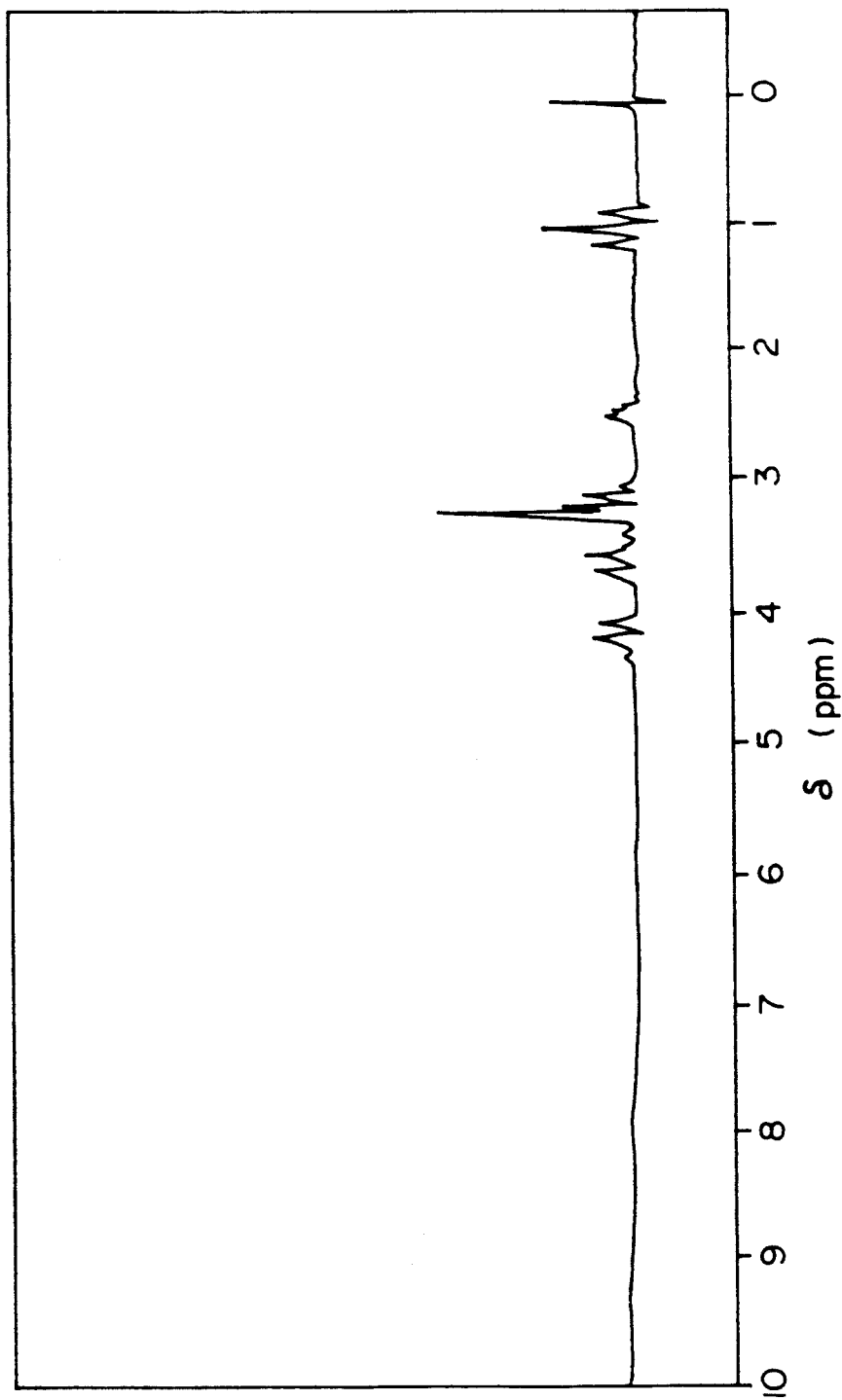
FIG. 2 is an NMR spectra of the product produced by Examiner 1A.

The product had a boiling point of 100° C. to 103° C./0.13 mmHg. The results of its IR and NMR measurements are shown in FIGS. 1 and 2. The mass spectrum of this product was 254. The elemental analysis values as found were C: 56.63%, H: 8.96% and N: 22.08%.

EXAMPLE 2A

Synthesis of N,N'-bis(2-oxazolinyl)-2,4-tolylenediamine

A solution of 40 parts of sodium hydroxide in 60 cc of water was added to a solution of 46.4 parts of 2-chloroethylamine hydrochloride in 60 cc of water with ice cooling and stirring, and the mixture was reacted for 30 minutes. The reaction mixture was extracted with 100 cc of ether three times. The extracts were dried over magnesium sulfate, and 34.0 parts of 4-tolylene diisocyanate was added. The mixture was heated under refluxing for 2 hours to give 62.7 parts of a white solid. Twenty-five parts of the resulting solid was added to a solution of 20 parts of potassium hydroxide in 700 cc of ethanol, and the mixture was heated under refluxing for 5 hours. The reaction mixture was hot-filtered, concentrated under reduced pressure, and recrystallized from methanol to give 6.8 parts of N,N'-bis(2-oxazolinyl)-2,4-tolylenediamine.

Figure 3:
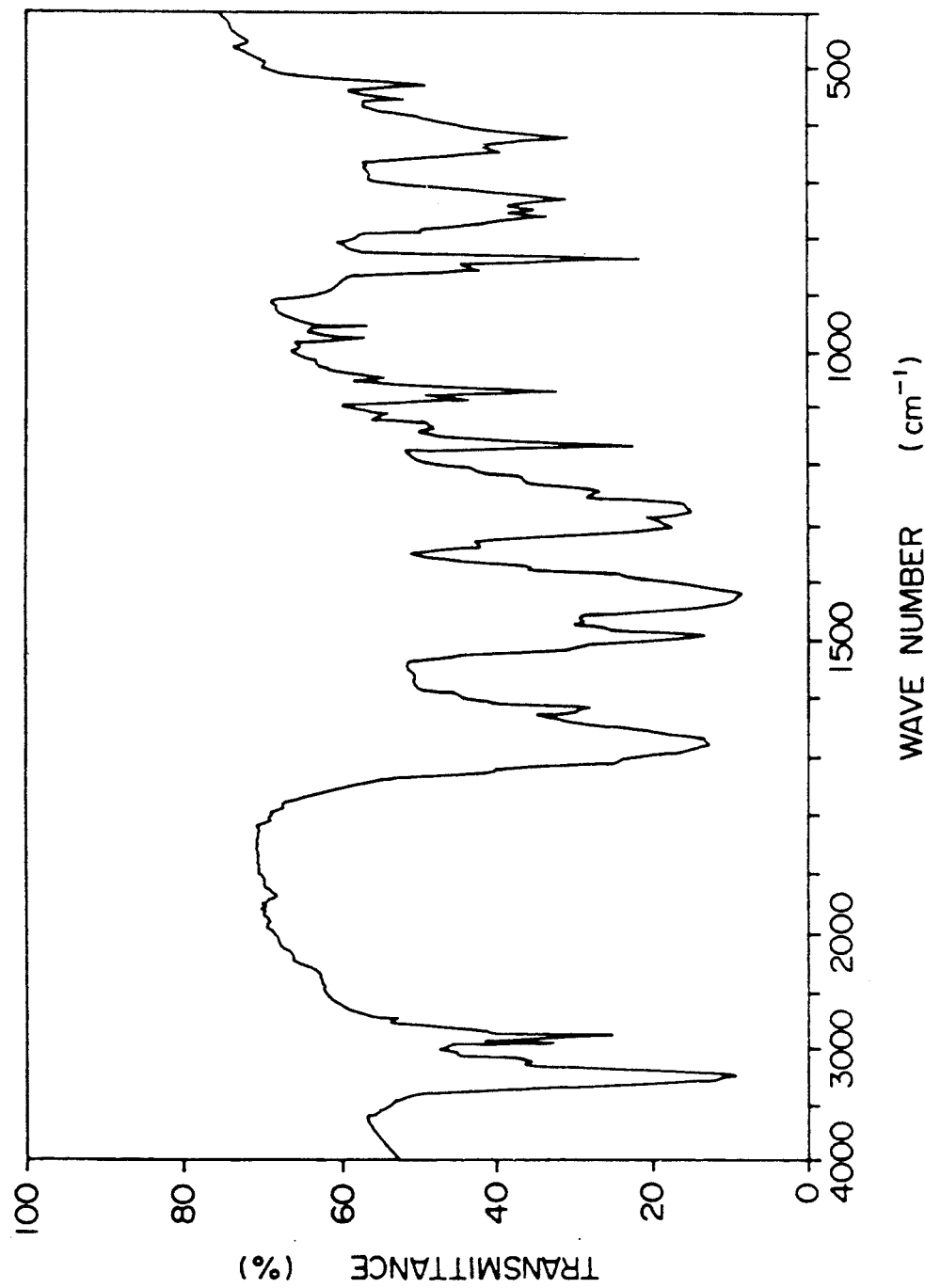
FIG. 3 is an IR spectra of the product produced in Example 2A.
Figure 4:
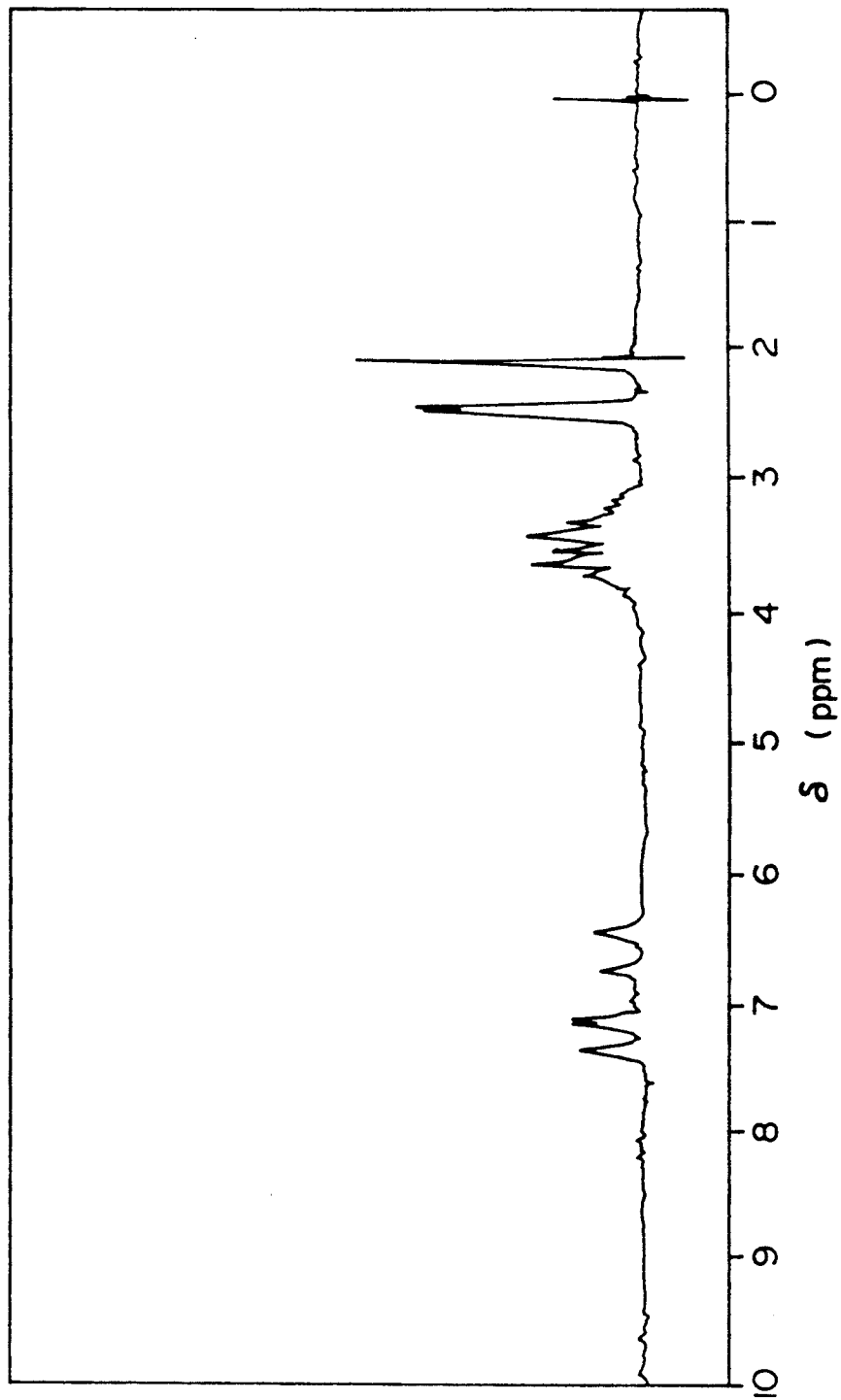
FIG. 4 is an NMR spectra of the product produced in Example 2A.

The melting point of the resulting product was 236° to 238° C. The results of its IR and NMR measurements are shown in FIGS. 3 and 4. Its mass spectrum was 260. The elemental analysis values as found were C: 60.00%, H: 6.03% and N: 21.45%.

EXAMPLE 3A

Synthesis of methylenebis[N-(2-oxazolinyl)aniline]

Forty-five parts of 4,4'-methylenedi(phenylisocyanate) was added to an ether solution of chloroethylamine obtained as in Example 2A, and the mixture was heated under refluxing for 2 hours to give 72.9 parts of a white solid. Fifty parts of the solid was added to a solution of 17.5 parts of potassium hydroxide in 650 cc of dimethyl sulfoxide, and the mixture was heated under refluxing for 5 hours. The reaction mixture was hot-filtered, and cooled to precipitate crystals. The crystals were collected by filtration, washed with water, and dried under reduced pressure to give 23.2 parts of methylenebis[N-(2-oxazolinyl)aniline].

Figure 5:
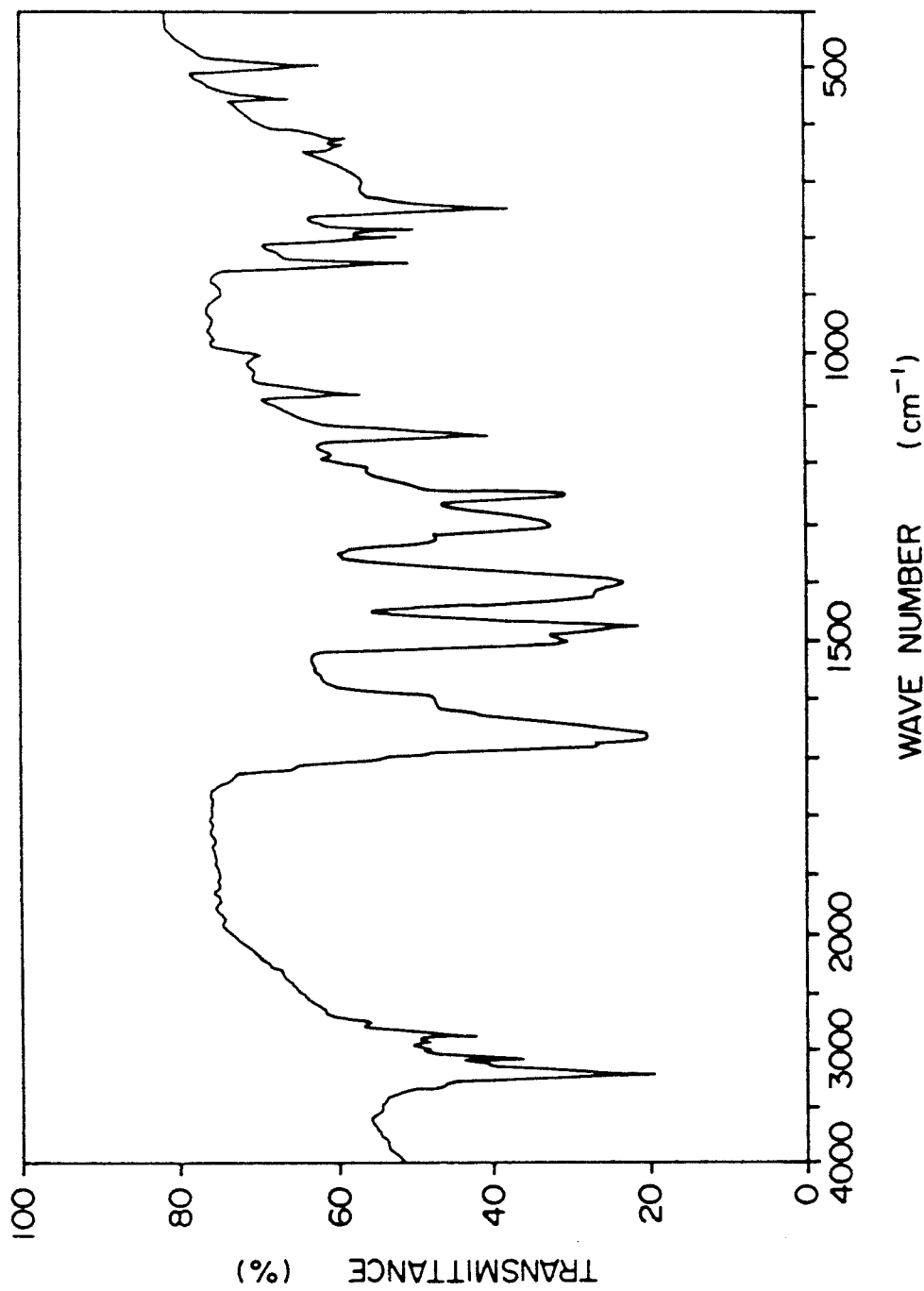
FIG. 5 is an IR spectra of the product produced in Example 3A.
Figure 6:
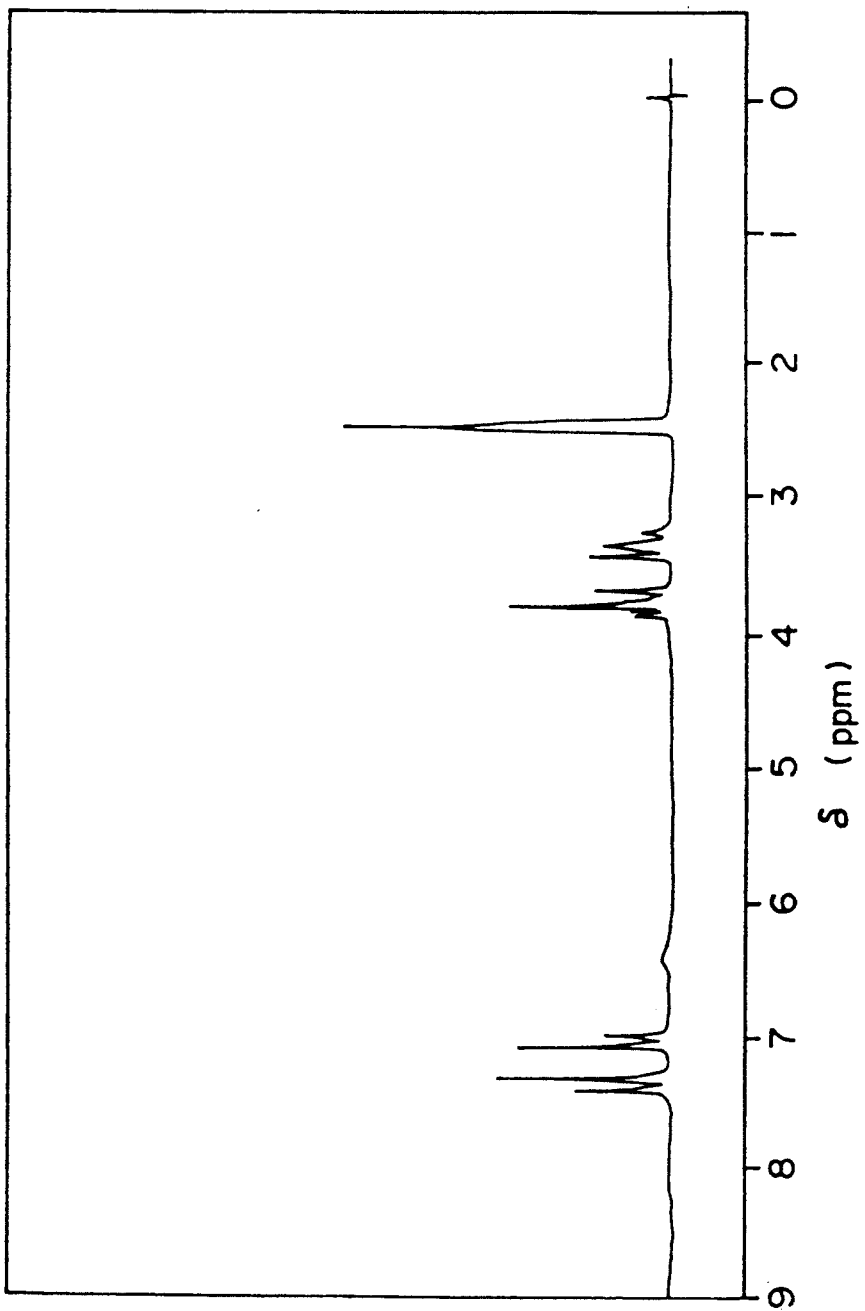
FIG. 6 is an NMR spectra of the product produced in Example 3A.

The melting point of the resulting product was more than 300° C., and the results of its IR and NMR measurements are shown in FIGS. 5 and 6. Its mass spectrum was 336. The elemental analysis values as found were C: 67.45%, H: 5.91% and N: 16.04%.

EXAMPLE 4A

Synthesis of N,N'-bis(2-oxazolinyl)hexamethylenediamine

A solution of 35.4 parts of potassium hydroxide in 150 cc of methanol was added with ice cooling and stirring to a solution of 58.0 parts of 2-chloroethylamine hydrochloride in 145 cc of methanol, and was reacted for 30 minutes. A solution of 40.0 parts of hexamethylenediisocyanate in 80 cc of methanol was added to the mixture and the mixture was heated under refluxing for 2 hours. A solution of 35.4 parts of potassium hydroxide in 150 cc of methanol was added to the mixture, and the mixture was heated under refluxing for 5 hours. The reaction mixture was hot-filtered, concentrated under reduced pressure and recrystallized from dioxane to give 28.2 parts of N,N'-bis(2-oxazolinyl)hexamethylenediamine.

Figure 7:
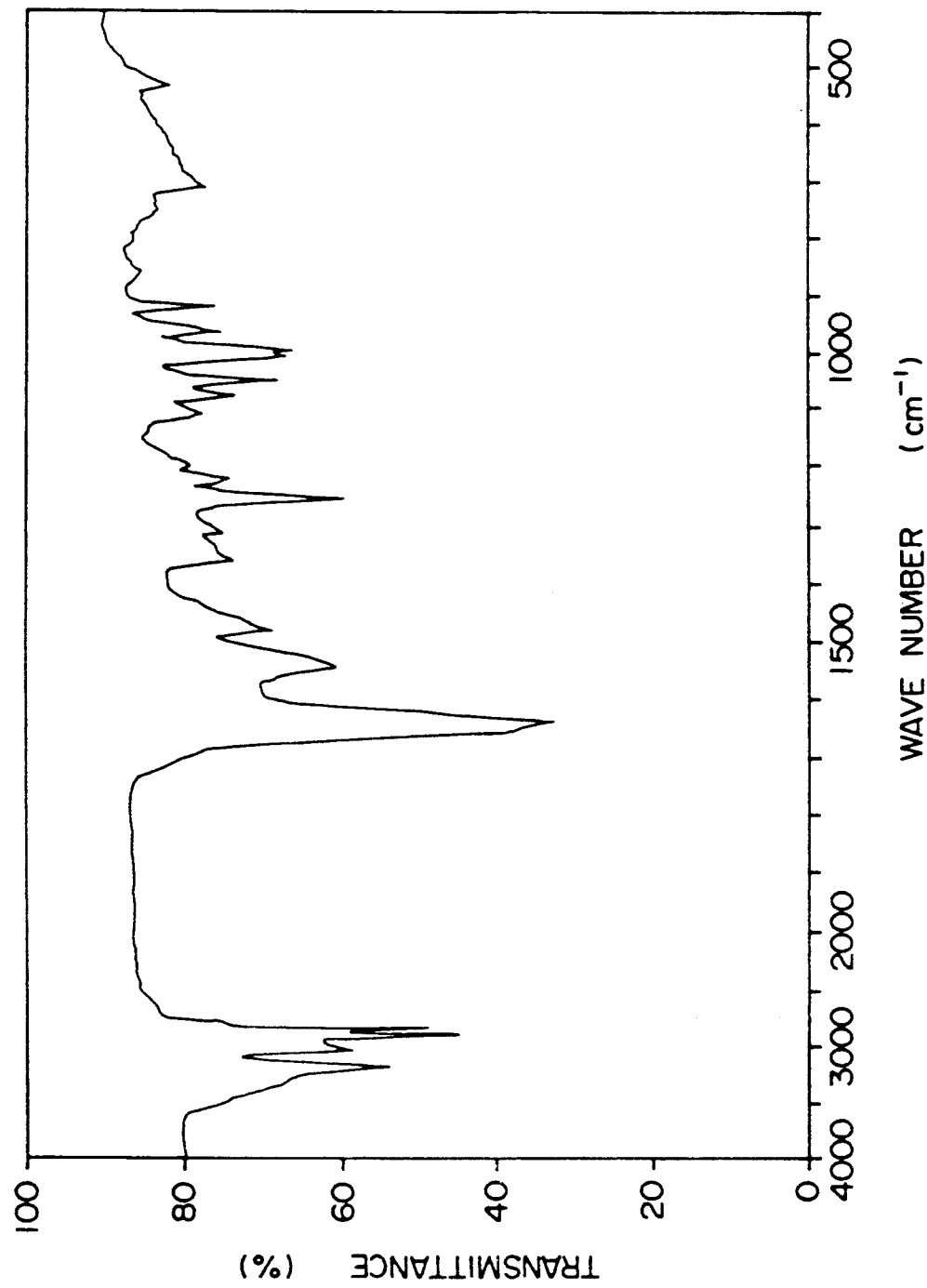
FIG. 7 is an IR spectra of the product produced in Example 4A.
Figure 8:
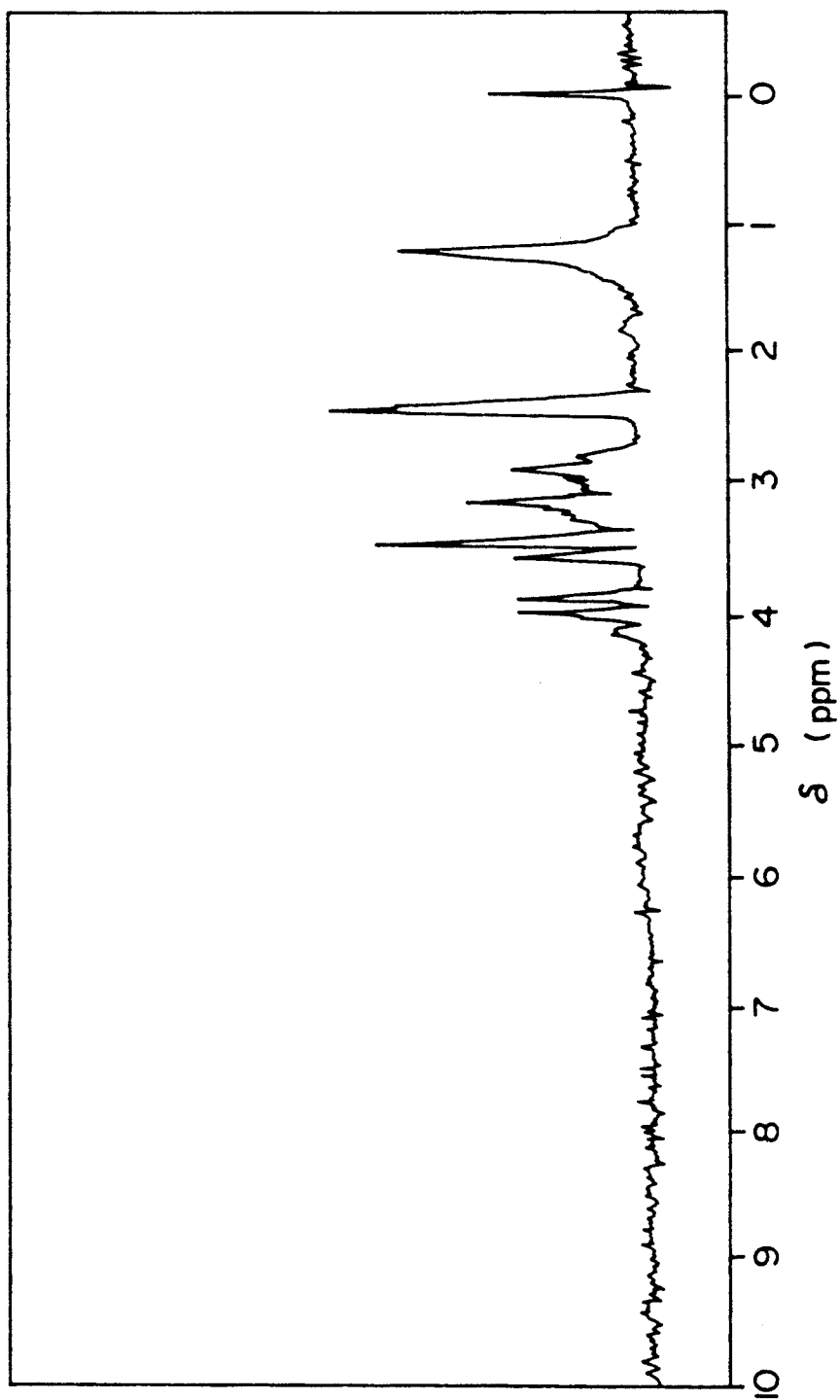
FIG. 8 is an NMR spectra of the product produced in Example 4A.

The melting point of the resulting product was 149° to 153° C. The results of its IR and NMR measurements are shown in FIGS. 7 and 8. Its mass spectrum was 254. The elemental analysis values as found were C: 56.72%, H: 8.77% and N: 21.03%.

EXAMPLE 5A

Test on the reactivity of N-oxazoline

N,N'-diethyl-N,N'-bis(2-oxazolinyl)ethylenediamine obtained in Example 1A was added to an unsaturated polyester having a COOH value of 1137 mol/ton and an OH value of 0 mol/ton, which had been synthesized from isophthalic acid, propylene glycol and maleic anhydride, in such an amount that the amount of the oxazoline ring was equivalent to the COOH value. The mixture was put in benzyl alcohol. After standing at 30° C. for 3 minutes the COOH value of the polyester became 520 mol/ton, and after standing at 90° C. for 10 minutes, it became 78 mol/ton. Separately, the above mixture was put in styrene. After standing at 30° C. for 1 minute, the ratio of the solution viscosity of (unsaturated polyester+poly(N-oxazoline)/the solution viscosity of the unsaturated polyester was 2.5. The results led to the determination that even at room temperature, the N-oxazoline compound shows high reactivity with COOH.

EXAMPLE 6A

Synthsis of N,N'-bis(2-oxazolinyl)-m-xylylenediamine 26.4 parts of m-xylylene diisocyanate was added to an ether solution of chloroethylamine obtained as in Example 2A, and the mixture was maintained in an ice bath for 2 hours to give 48.5 parts of a white solid. Forty parts of the resulting solid and 16.2 parts of potassium methoxide were added to 500 cc of methanol, and with stirring, the mixture was heated under refluxing for 5 hours. The reaction mixture was filtered, and the filtrate was concentrated. The precipitated salt was separated by filtration while it was still flowable. The filtrate was poured into 200 cc of acetone, and the precipitated solid was separated by filtration. The filtrate was concentrated under reduced pressure and poured into a mixture of 1 cc of ethyl acetate and 200 cc of acetone to give 19 parts of a white solid. The solid was recrystallized from tetrahydrofuran (THF) to give 12 parts of N,N'-bis(2-oxazolinyl)-m-xylylenediamine.

Figure 9:
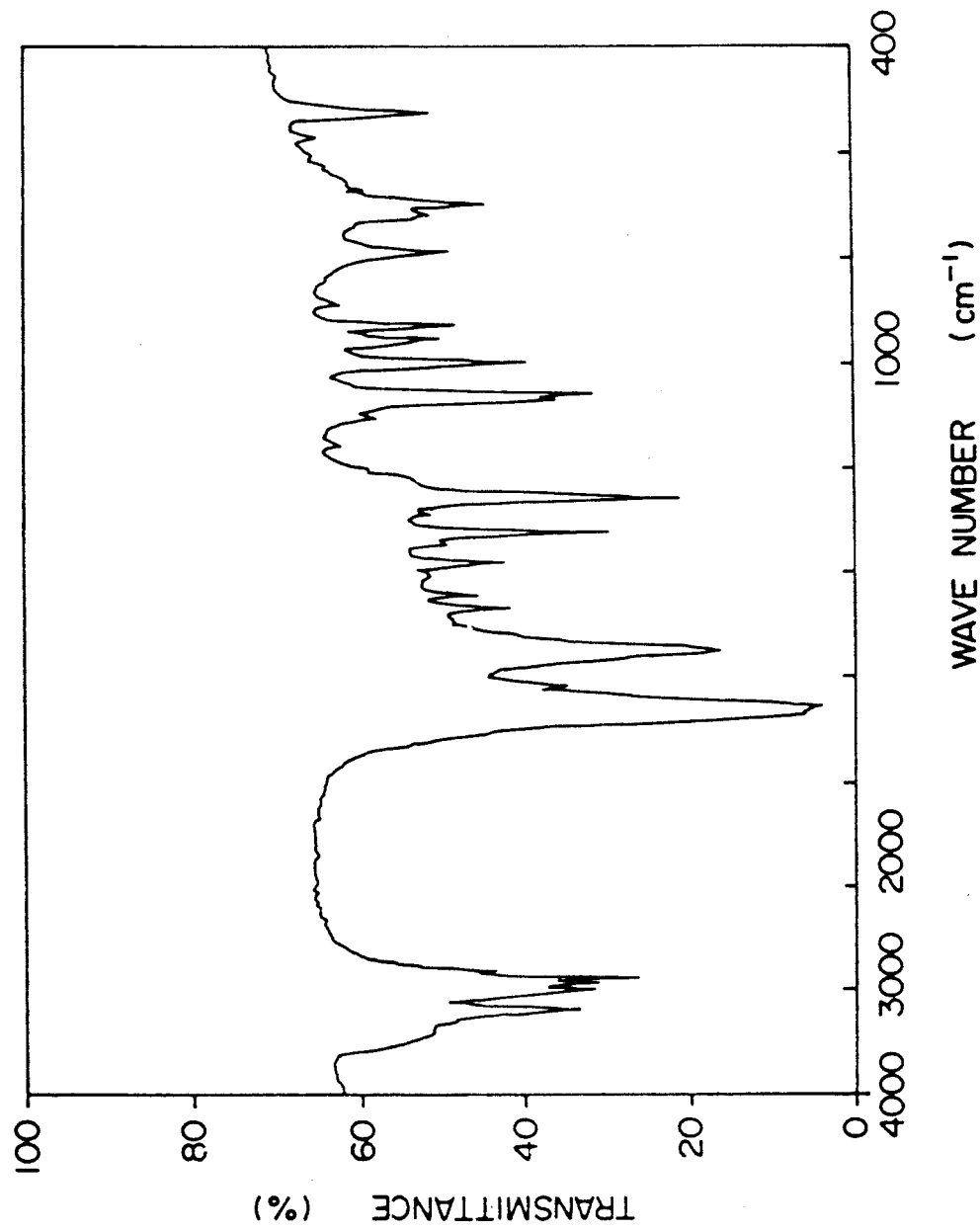
FIG. 9 is an IR spectra of the product produced in Example 6A.
Figure 10:
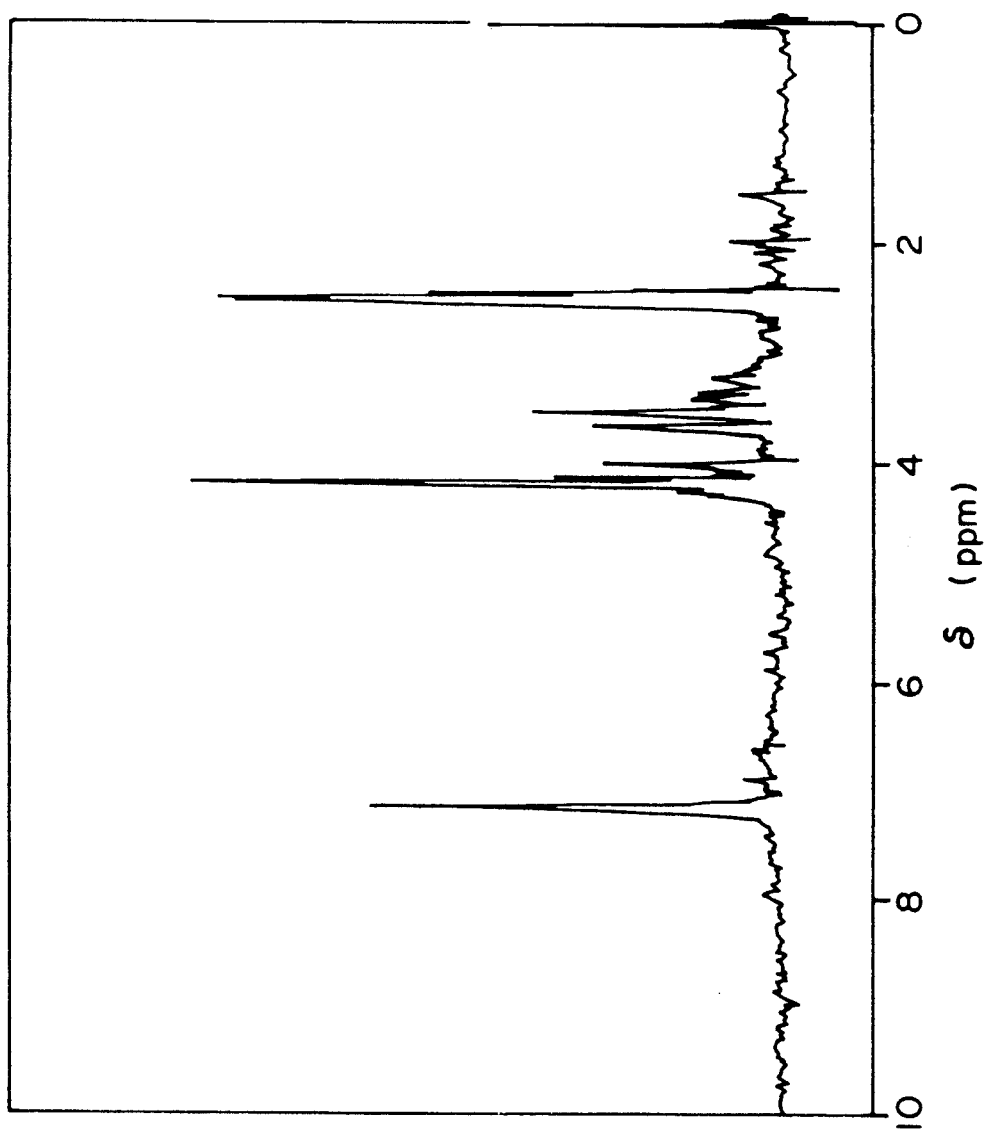
FIG. 10 is an NMR spectra of the product produced in Example 6A.

The melting point of the resulting product was 143° to 145° C., and the results of its IR and NMR measurements are shown in FIGS. 9 and 10.

The mass spectrum of this product was 274, and its elemental analysis values as found were C: 61.34%, H: 6.53% and N: 20.38%.

EXAMPLE 7A

Synthesis of 1,3-bis(2-oxazolinylaminomethyl)cyclohexane 27.0 parts of 1,3-bis(isocyanatemethyl)cyclohexane was added to an ether solution of chloroethylamine obtained as in Example 2A, and the mixture was maintained in an ice bath for 2 hours to give 48.9 parts of a white solid. Thirty parts of the resulting solid was added to a solution of 9.5 parts of potassium hydroxide in 500 cc of methanol, and the mixture was heated under refluxing for 5 hours. The reaction mixture was filtered. Ethyl acetate (0.5 cc) was added to the filtrate and the mixture was concentrated. Ethanol (65 cc) was added to the concentrate. The mixture was filtered, and the filtrate was concentrated under reduced pressure. The concentrate was added to 72 cc of acetone. The precipitate was collected by filtration. The filtrate was left to stand in an ice bath to give 18 parts of crystals.

Figure 11:
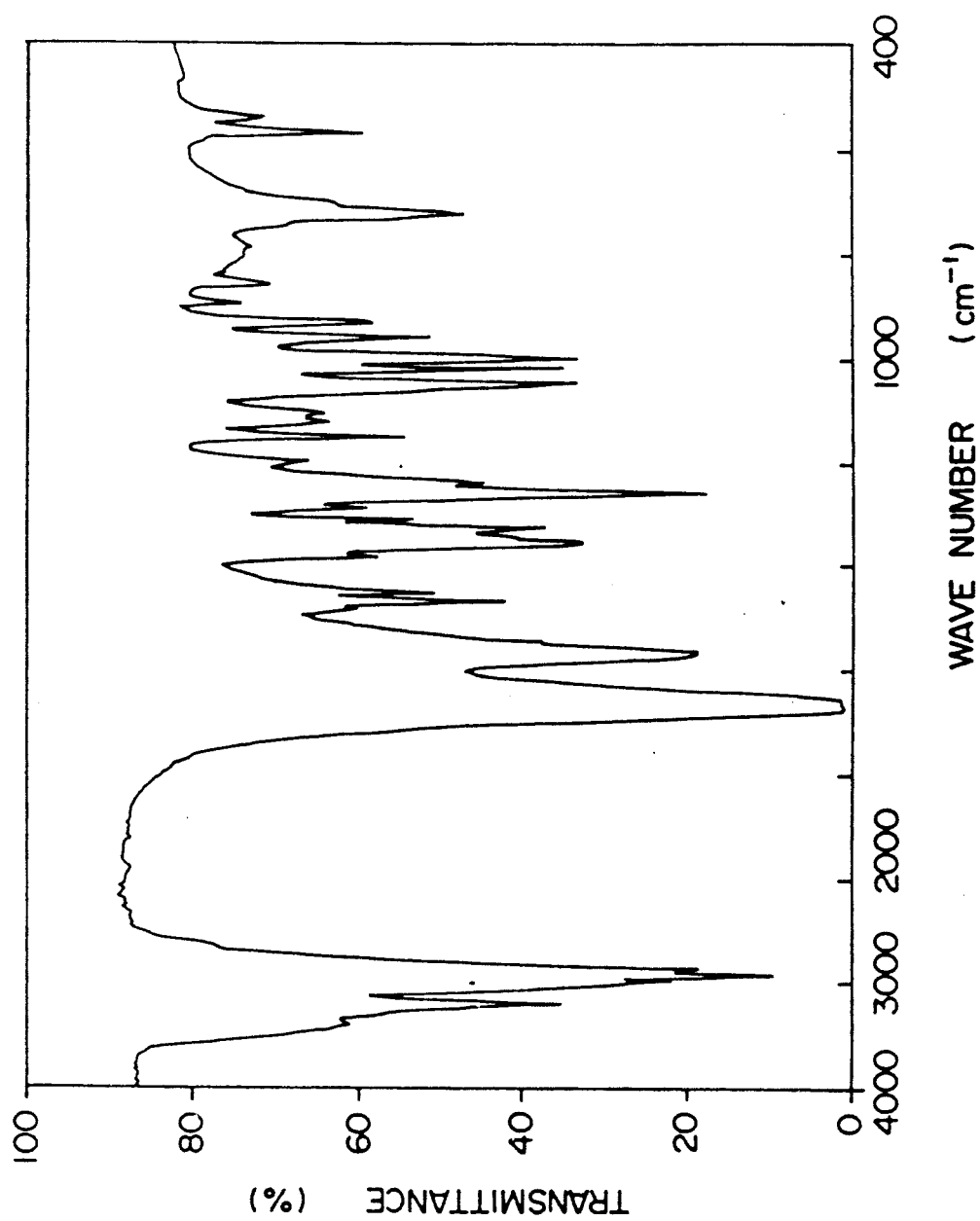
FIG. 11 is an IR spectra of the product produced in Example 7A.
Figure 12:
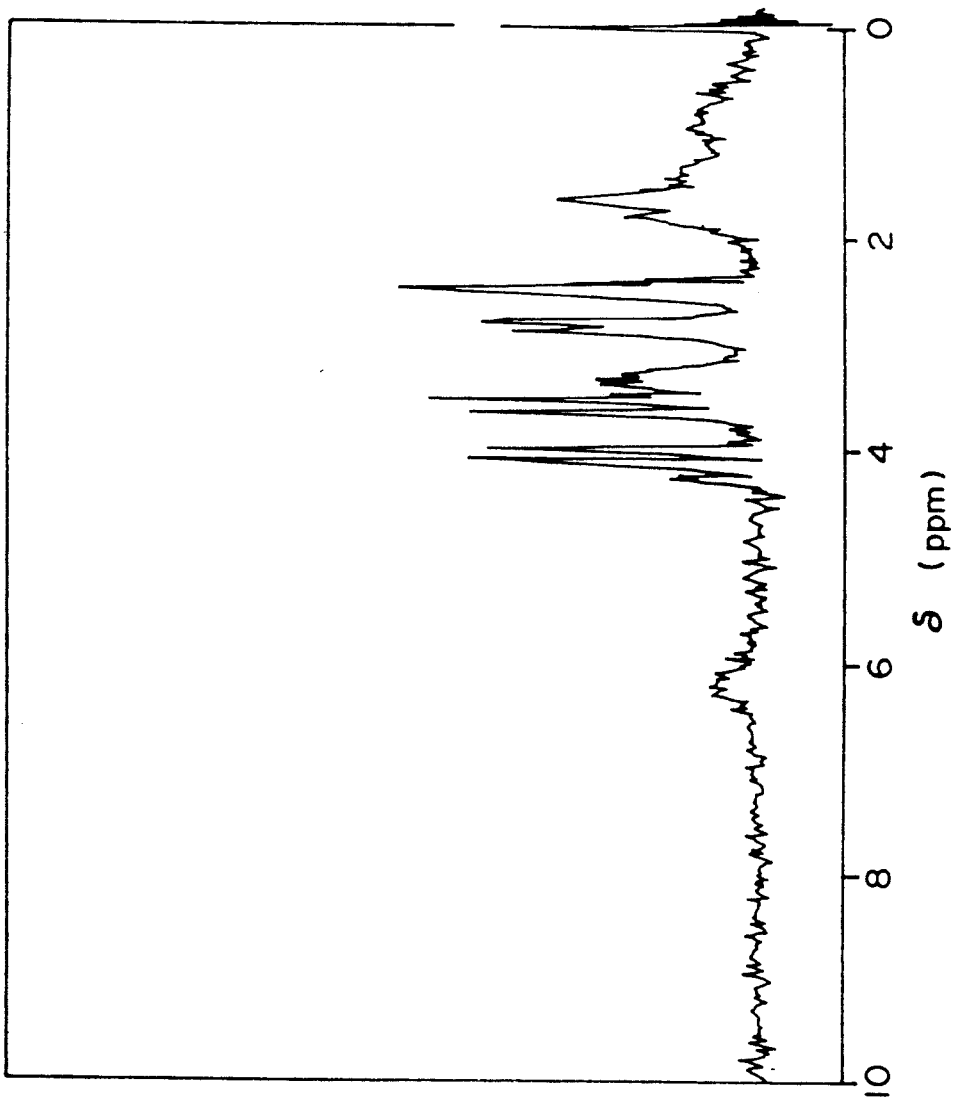
FIG. 12 is an NMR spectra of the product produced in Example 7A.

The crystals were recrystallized from THF to give 11 parts of 1,3-bis(2-oxazolinylaminomethyl)cyclohexane. The melting point of this product was 136° to 139° C. The results of its IR and NMR measurements are show in FIGS. 11 and 12.

The mass spectrum of this product was 280, and its elemental analysis values as found were C: 59.89%, H: 8.64%, and N: 19.90%.

EXAMPLE 8A

Figure 13:
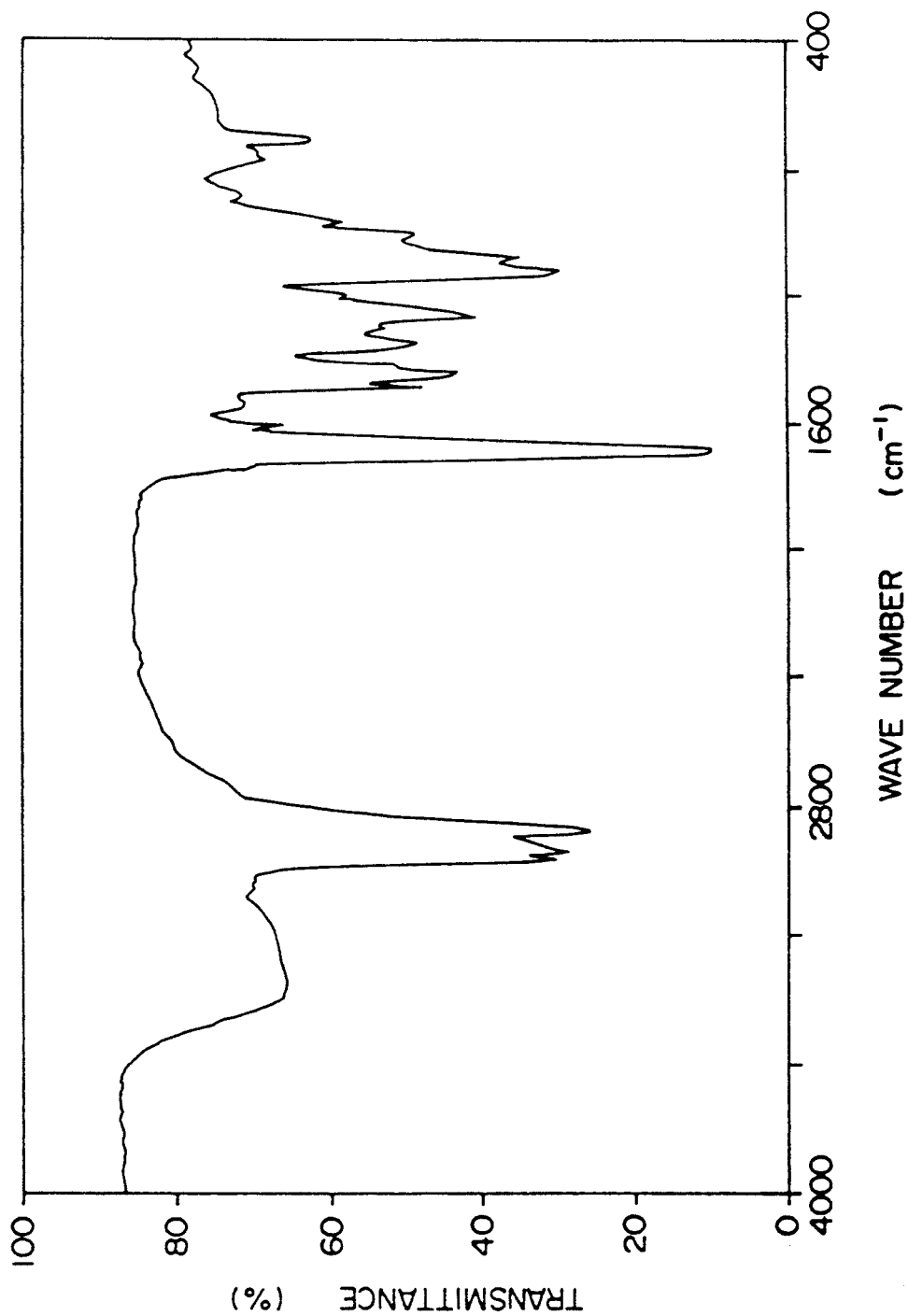
FIG. 13 is an IR spectra of the product produced in Example 8A.
Figure 14:
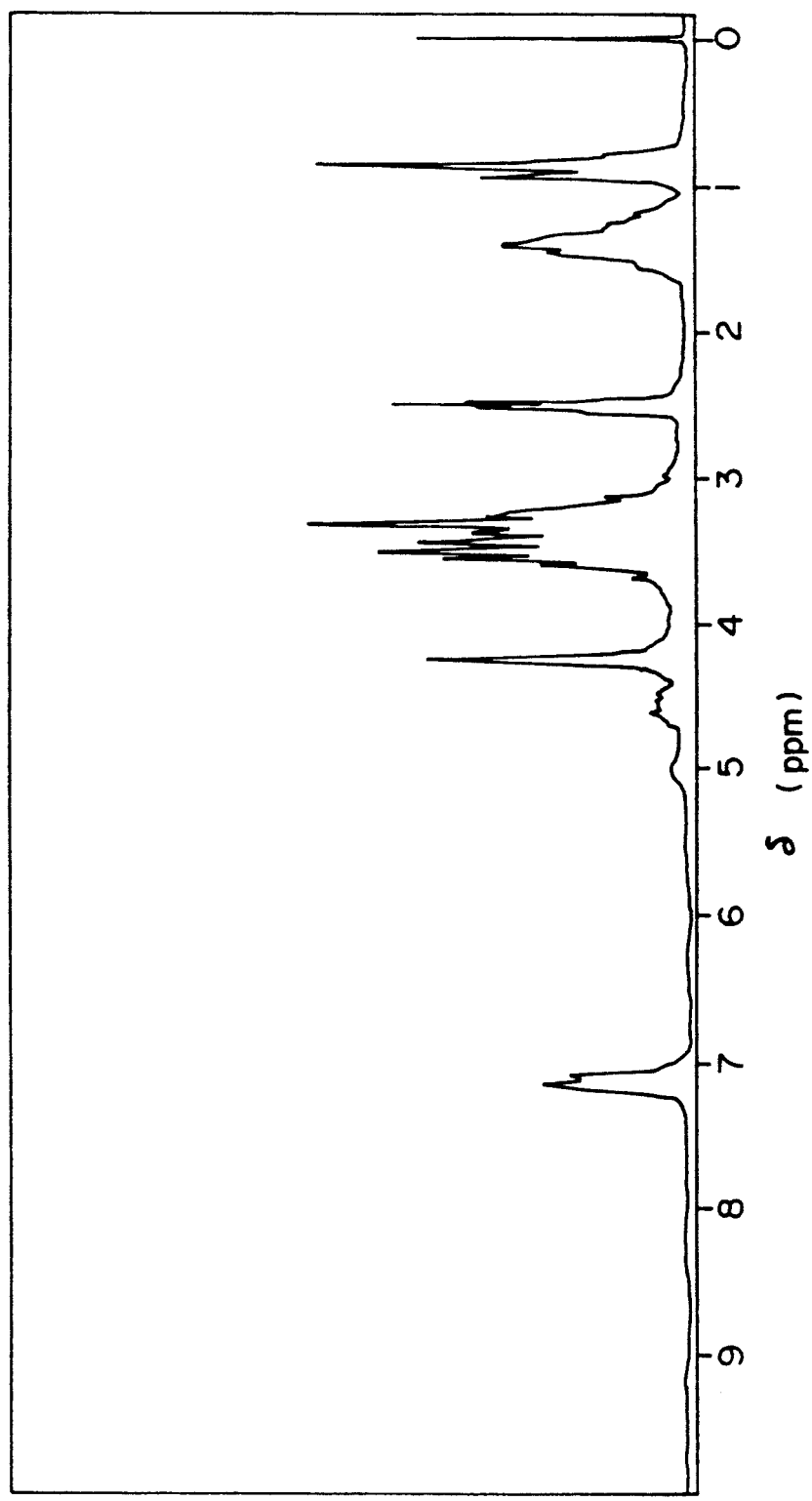
FIG. 14 is an NMR spectra of the product produced in Example 8A.

Synthesis of N,N'-bis(2-oxazolinyl)-N,N'-bis(3-butoxy-2-hydroxypropyl)-m-xylylenediamine Butyl glycidyl ether (26.0 parts) was added to 27.4 parts of N,N'-bis(2-oxazolinyl)-m-xylylenediamine obtained in Example 6A, and the mixture was reacted at 150° C. for 1 hour under a nitrogen atmosphere with stirring to give a pale yellow viscous liquid. The epoxy equivalent of this liquid was found to be 2241 g/eq. The results of its IR and NMR measurements shown in FIGS. 13 and 14 show that 88% N,N'-bis(2-oxazolinyl)-N,N'-bis(3-butoxy-2-hydroxypropyl)-m-xylylenediamine was synthesized.

EXAMPLE 9A

Synthesis of N,N'-bis(2-oxazolinyl-3,4'-diaminodiphenylether

A solution of 38.0 parts of 3,4'-diaminodiphenylether in 200 parts of methylene chloride was added dropwise with ice cooling over 10 minutes to a solution of 40 parts of chloroethyl isocyanate in 222 parts of methylene chloride, and the mixture was maintained at room temperature for 2 hours. It was further heated under reflux for 1 hour. After the reaction, the precipitated solid was collected by filtration and then dried under reduced pressure to give 70.0 parts of a pale brown solid. The resulting solid (61.7 parts) was added to a solution of 21.0 parts of potassium methoxide in 1 liter of methanol. The mixture was heated under refluxing for 12 hours. A solid was recovered by filtration from the reaction mixture, washed with water and then recrystallized from dimethyl sulfoxide to give 22.8 parts of N,N'-bis(2-oxazolinyl)-3,4'-diaminodiphenyl ether.

Figure 15:
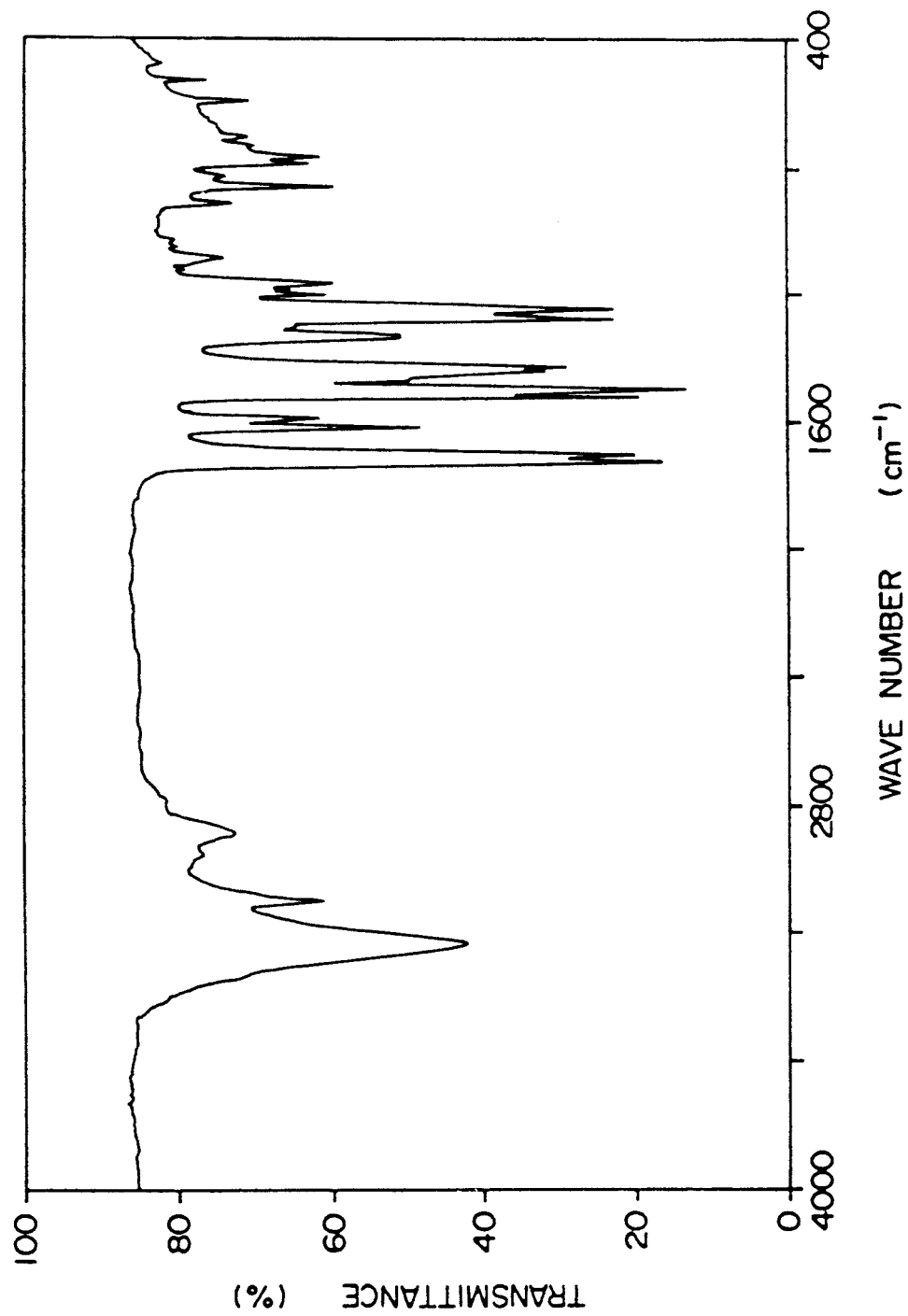
FIG. 15 is an IR spectra of the product produced in Example 9A.
Figure 16:
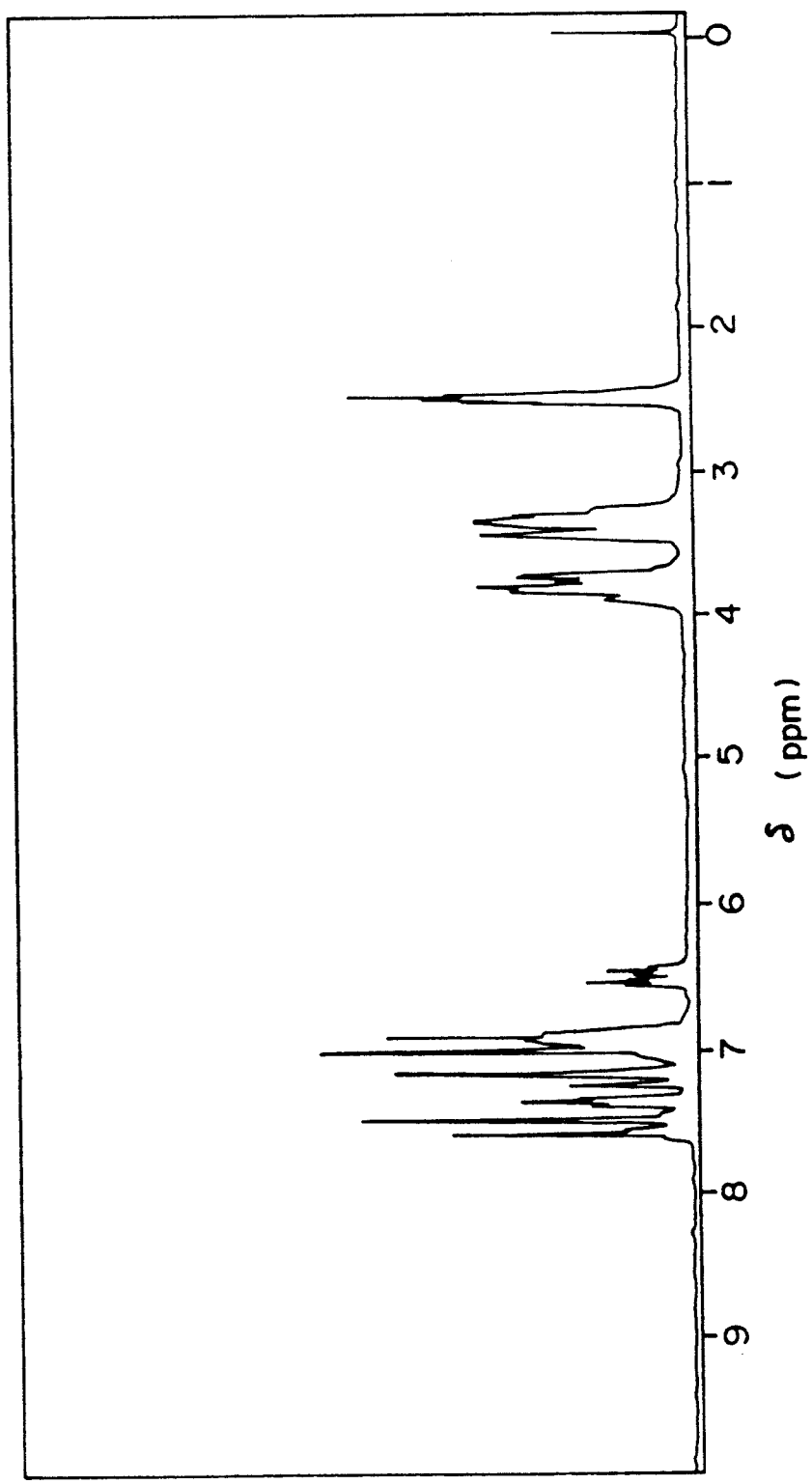
FIG. 16 is an NMR spectra of the product produced in Example 9A.

The melting point of the resulting product was 280° to 283° C., and the results of its IR and NMR measurements are shown in FIGS. 15 and 16. Its mass spectrum was 338, and the elemental analysis values as found were C: 63.80%, H: 5.33% and N: 16.49%.

EXAMPLE 10A

Synthesis of N,N',N''-tris(2-oxazolinyl)diethylenetriamine

A solution of 13.0 parts of diethylenetriamine in 30 parts of methylene chloride was added dropwise with ice cooling over 20 minutes to a solution of 40 parts of chloroethyl isocyanate in 220 parts of methylene chloride. The mixture was reacted for 2 hours, and then at room temperature for 2 hours, and further under refluxing for 1 hour. After the reaction, the precipitated solid was collected by filtration and then dried under reduced pressure to give 51.0 parts of a white solid.

The resulting solid (42.0 parts) was added to a solution of 21.0 parts of potassium methoxide in 600 cc of methanol, and the mixture was heated under refluxing for 5 hours. The reaction mixture was filtered, and the filtrate was concentrated under reduced pressure. The precipitated salt was separated while it was still flowable, and poured into 100 cc of acetone. The precipitated solid was separated by filtration. The filtrate was concentrated under reduced pressure, and the resulting white solid was recrystallized from dioxane to give 4.7 parts of N,N',N''-tris(2-oxazolinyl)diethylenetriamine.

Figure 17:
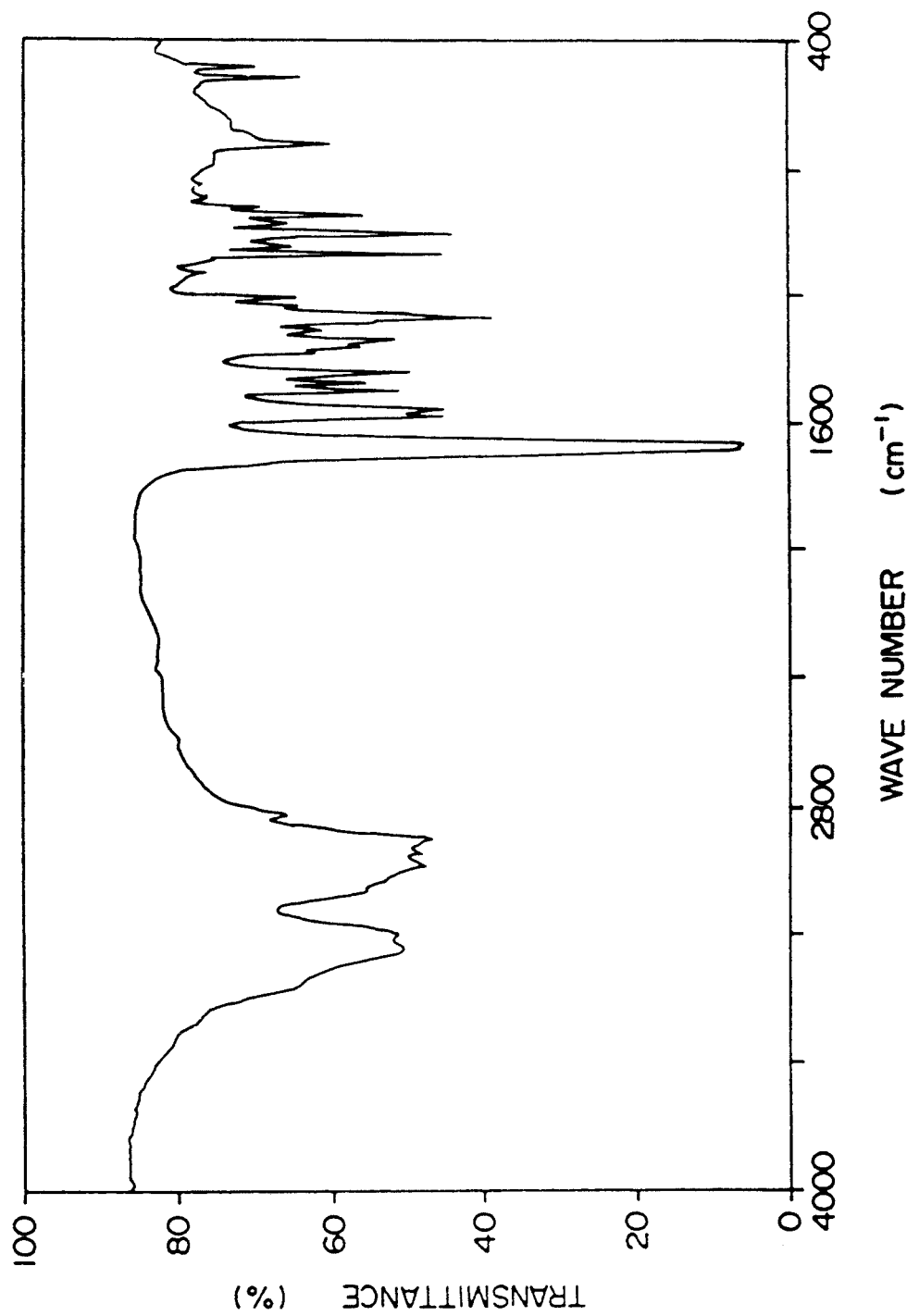
FIG. 17 is an IR spectra of the product produced in Example 10A.
Figure 18:
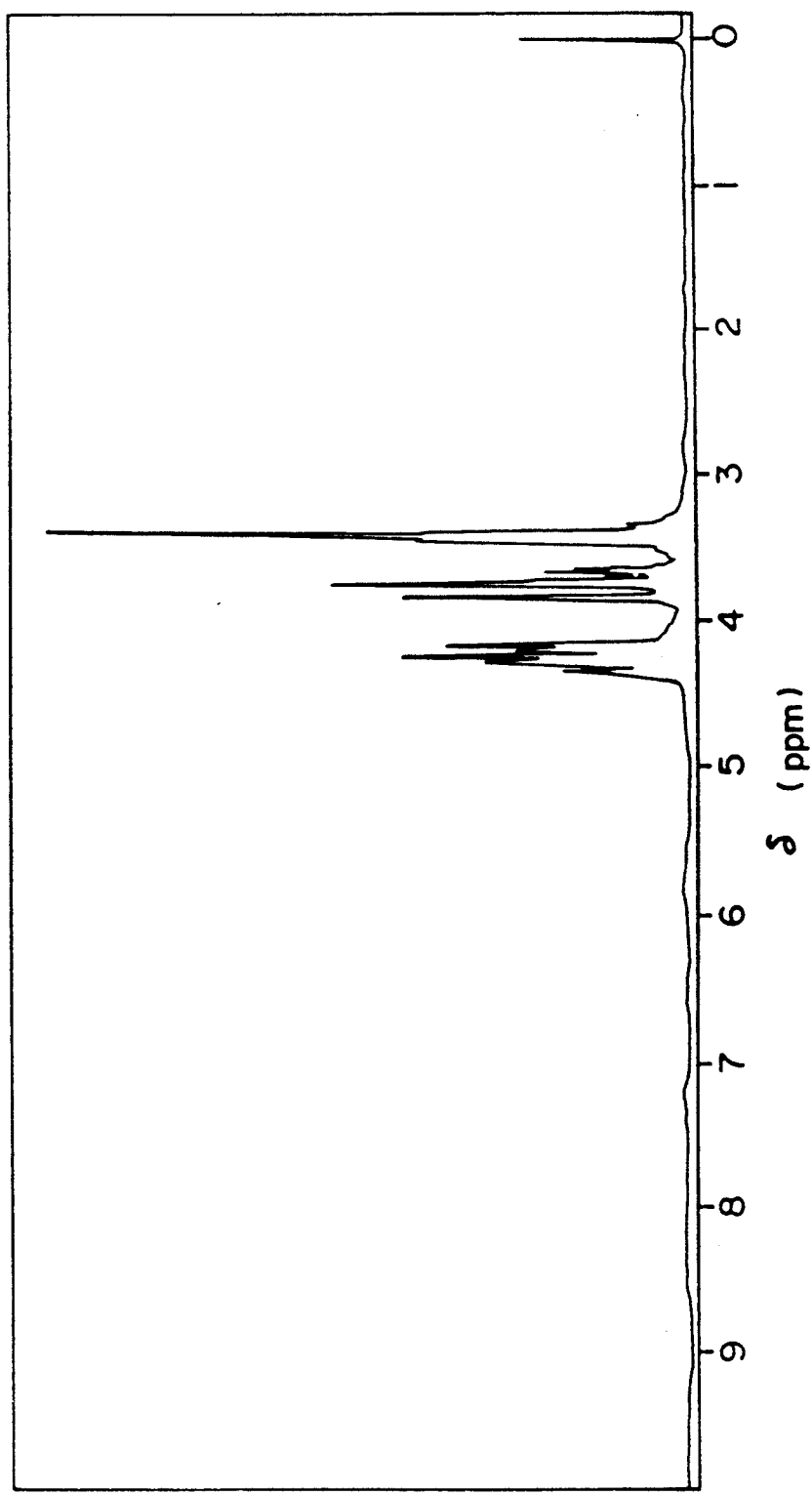
FIG. 18 is an NMR spectra of the product produced in Example 10A.

This product had a melting point of 103° to 106° C. The results of its IR and NMR measurements are shown in FIGS. 17 and 18. The NMR of this compound was measured in d-chloroform.

Its mass spectrum was 310, and its elemental analysis values as found were C: 50.26%, H: 7.11% and N: 26.99%.

EXAMPLE 11A

Synthesis of N,N'-bis(5,6-dihydro-4H-oxazinyl)-m-xylylenediamine

Ether (185 cc) was added to a solution of 65 parts of 3-chloropropylamine hydrochloride in 75 cc of water, and a solution of 50 parts of sodium hydroxide in 75 cc of water was added with ice cooling and stirring. The mixture was reacted for 1 hour. The reaction mixture was extracted with 100 cc of ether three times. The extracts were dried over sodium sulfate, and a solution of 33 parts of m-xylylene diisocyanate in 34.0 parts of methylene chloride was added with ice cooling and stirring. The mixture was reacted for 2 hours to give 41.9 parts of a white solid. The resulting solid (37.4 parts) and 14.0 parts of potassium methoxide were added to 550 cc of methanol, and with stirring, the mixture was heated under refluxing for 5 hours. The reaction mixture was filtered, and the filtrate was concentrated under reduced pressure. The precipitated salt was separated by filtration while it was still flowable. The filtrate was poured into 50 cc of acetone, and the precipitated solid was separated by filtration. The filtrate was concentrated under reduced pressure, and the resulting solid was recrystallized from THF to give 6.2 parts of white crystals.

When the mass spectrum of the crystals was measured, its parent peak was 302. This showed that N,N'-bis(5,6-dihydro-4H-oxazinyl)-m-xylylenediamine was synthesized.

EXAMPLE 1B AND COMPARATIVE EXAMPLES 1B and 2B

A glass vessel was charged with 2.73 parts of N,N'-bis(2-oxazolinyl)-m-xylylenediamine and 7.90 parts of bisphenol A-type epoxy resin having an epoxy equivalent of 190 g/eq. After the inside of the glass vessel was purged with nitrogen at room temperature, the mixture was heated to 175° C. The reaction mixture first uniformly dissolved and then reacted and cured in each of the time periods indicated in Table 1 to give a pale yellow resin. The resulting resin had no foam and was insoluble in acetone and other organic solvents.

For comparison, 4.32 parts of 2,2'-m-phenylenebis(2-oxazoline) or 2.48 parts of 3,3'-diaminodiphenylsulfone was used instead of N,N'-bis(2-oxazolinyl)-m-xylylenediamine in the above procedure. The results show that the N-oxazoline had very high reactivity.

TABLE 1

|  | Compound (A) | Reaction temperature (°C.) | Curing time |
|---|---|---|---|
| Example 1B | N,N'-bis(2-oxazolinyl)-m-xylylenediamine | 175 | 36 seconds |
| Comparative Example 1B | 2,2'-m-phenylene-bis(2-oxazoline) | 200 | 17 minutes 40 seconds |
| Comparative Example 2B | 3,3'-diaminodiphenylsulfone | 200 | 2 minutes 57 seconds |

EXAMPLE 2B AND COMPARATIVE EXAMPLES 3B and 4B

N,N'-bis(2-oxazolinyl)-m-xylylenediamine and bisphenol A-type epoxy resin having an epoxy equivalent of 190 g/eq. were used in the same proportions as in Example 1B, and the molding shrinkage of the product was determined by the specific gravity method. The results are shown in Table 2.

For comparison, the above procedure was repeated except that 2,2'-m-phenylenebis(2-oxazoline) or 3,3'-diaminodiphenylsulfone was used in the same proportion as in Comparative Examples 1B and 2B. The molding shrinkages are shown in Table 2. The results show that the molding shrinkage of the N-oxazoline was low.

TABLE 2

|  | Compound (A) | Measuring temperature (°C.) | Molding shrinkage (%) |
|---|---|---|---|
| Example 2B | N,N'-bis(2-oxazolinyl)-m-xylylenediamine | 175 | 2.0 |
| Comparative Example 3B | 2,2'-m-phenylene-bis(2-oxazoline) | 200 | 5.1 |
| Comparative Example 4B | 3,3'-diaminodiphenylsulfone | 200 | 3.7 |

EXAMPLE 3B AND COMPARATIVE EXAMPLE 5B

A glass vessel was charged with 27.3 parts of N,N'-bis(2-oxazolinyl)-m-xylylenediamine and 79.0 parts of bisphenol A-type epoxy resin having an epoxy equivalent of 190 g/eq. The inside of the glass vessel was purged with nitrogen at room temperature, and then the mixture was heated to 150° C. to form a uniform solution. The solution was injected into a mold heated in advance to 175° C., and reacted for 15 minutes. The resulting molded plate was taken out, and its impact strength and heat resistance were measured by using an Izod impact strength tester and HDT & V.S.P.G tester made by Toyo Seiki Seisakusho. The results are shown in Table 3.

For comparison, the above procedure was repeated except that 43.2 parts of 2,2'-m-phenylenebis(2-oxazoline) was used instead of N,N'-bis(2-oxazolinyl)-m-xylylenediamine used in Example 3B, the temperature of the mold was changed to 200° C., and the reaction time was changed to 70 minutes. The results are shown in Table 3.

The results show that the moldd article obtained by using the N-oxazoline had high impact strength and heat resistance.

TABLE 3

| | Compound (A) | Izod notched impact strength (kg-cm/cm) | Heat distortion temperature (°C.) |
|---|---|---|---|
| Example 3B | N,N'-bis(2-oxazolinyl)-m-xylylenediamine | 3.7 | 137 |
| Comparative Example 5B | 2,2'-m-phenylenebis-(2-oxazoline) | 2.5 | 101 |

EXAMPLE 4B

A glass vessel was charged with 16.4 parts of N,N'-bis(2-oxazolinyl)-m-xylylenediamine and 15.2 parts of bisphenol A-type epoxy resin having an epoxy equivalent of 190 g/eq. The inside of the glass vessel was purged with nitrogen, and then heated to 150° C. to form a uniform solution. Then, 0.95 part of ethyl p-toluenesulfonate was added to the solution. The reaction mixture cured in 85 seconds and became a colorless transparent resin. The resin had no foam and was insoluble in acetone and other organic solvents. It had high heat resistance as shown by its heat distortion temperature of 140° C.

EXAMPLES 5B to 7B

In each run, a glass vessel was charged with 7.9 parts of bisphenol A-type epoxy resin having an epoxy equivalent of 190 g/eq. and each of the poly(N-cyclic iminoether) compounds in the indicated amount in Table 4. After purging with nitrogen at room temperature, the mixture was heated to 175° C. The resin first dissolved uniformly and then cured in each of the time periods indicated in Table 4 to a pale yellow to yellow resin.

The resins obtained had no foam, and were insoluble in acetone and other organic solvents. Table 4 shows the heat distortion temperatures of the resins. These resins were found to have high heat resistance.

TABLE 4

| Example | Poly(N-cyclic iminoether) (parts) | Curing time | Heat distortion temperature (°C.) |
|---|---|---|---|
| 5B | N,N'-bis(2-oxazolinyl)-hexamethylenediamine (2.6) | 3 min. 50 sec. | 120 |
| 6B | 1,3-bis(2-oxazolinyl-aminomethyl)cyclohexane (2.9) | 2 min. 15 sec. | 156 |
| 7B | N,N',N''-tris(2-oxazolinyl)-diethylenetriamine (2.6) | 1 min. 3 sec. | 110 |

EXAMPLES 8B to 10B

In each run, a glass vessel was charged with 7.2 parts of phenol novolak-type epoxy resin having an epoxy equivalent of 179 g/eq. and each of the poly(N-oxazoline)s shown in Table 5 in the indicated amount. After purging with nitrogen at room temperature, the mixture was heated to each of the reaction temperatures indicated in Table 5. The reaction mixture first dissolved uniformly and then cured in each of the curing times indicated in Table 5 to a colorless to pale yellow resin.

The resins obtained in these examples had no foam and were insoluble in acetone and other organic solvents. The heat distortion temperatures of the resulting resin shown in Table 5 demonstrate the high heat resistance of these resins.

TABLE 5

| Example | Poly(N-oxazoline) (parts) | Reaction temperature (°C.) | Curing time | HDT (°C.) |
|---|---|---|---|---|
| 8B | N,N'-bis(2-oxazolinyl)-m-xylylenediamine (2.7) | 150 | 50 sec. | 145 |
| 9B | N,N'-bis(2-oxazolinyl)-m-xylylenediamine (5.5) | 150 | 36 sec. | 135 |
| 10B | 1,3-bis(2-oxazolinyl-aminomethyl)cyclo-hexane (2.8) | 175 | 2 min. 30 sec. | 156 |

EXAMPLES 11B and 12B

In each run, a glass vessel was charged with 17.57 parts of tris(hydroxyphenyl)methane triglycidyl ether having an epoxy equivalent of 162 g/eq. and each of the poly(N-oxazoline)s shown in Table 6 in the indicated amount. After purging with nitrogen at room temperature, the mixture was heated to 175° C. The reaction mixture first dissolved uniformly, and cured in each of the times shown in Table 6 to an orange resin.

The resulting resins had no foam, and were insoluble in acetone and other organic solvents. The heat distortion temperatures of the resulting resins shown in Table 6 demonstrate the high heat resistance of these resins.

TABLE 6

| Example | Poly(N-oxazoline) (parts) | Curing time | Heat distortion temperature (°C.) |
|---|---|---|---|
| 11B | N,N'-bis(2-oxazolinyl)-m-xylylenediamine | 62 sec. | 240 |

TABLE 6-continued

| Example | Poly(N-oxazoline) (parts) | Curing time | Heat distortion temperature (°C.) |
|---|---|---|---|
| 12B | (7.4) 1,3-bis(2-oxazolinyl-aminomethyl)cyclohexane (7.6) | 2 min. 40 sec. | 232 |

EXAMPLES 13B to 16B

In each run, a glass vessel was charged with 2.7 parts of 2,2'-m-phenylenebis(2-oxazoline) and each of the poly(N-oxazoline)s and each of the epoxy compounds shown in Table 7 in the indicated amounts. After purging with nitrogen at room temperature, the mixture was heated to 175° C. The reaction mixture first dissolved uniformly. Then, 0.8 part of p-toluenesulfonic acid was added. The reaction mixture then cured in each of the time periods indicated in Table 7 to a colorless to pale orange resin.

The resulting resins had no foam, and were insoluble in acetone and other organic solvent. The heat distortion temperatures of the resulting resins shown in Table 7 demonstrate the high heat resistance of these resins.

TABLE 7

| Example | Poly(N-oxazoline) (parts) | Polyepoxy compound (parts) | Curing time | HDT (°C.) |
|---|---|---|---|---|
| 13B | N,N'-bis(2-oxazolinyl)-m-xylylenediamine (6.9) | phenol novolak type epoxy* (17.9) | 2 min. | 155 |
| 14B | N,N'-bis(2-oxazolinyl)-m-xylylenediamine (6.9) | bisphenol A-type epoxy** (17.9) | 1 min. 40 sec. | 143 |
| 15B | 1,3-bis(2-oxazolinyl-aminomethyl)cyclohexane (7.1) | phenol novolak-type epoxy* (17.9) | 3 min. 40 sec. | 151 |
| 16B | 1,3-bis(2-oxazolinyl-aminomethyl)cyclohexane (7.1) | bisphenol A-type epoxy** (19.0) | 3 min. 10 sec. | 139 |

*epoxy equivalent 179 g/eq.
**epoxy equivalent 190 g/eq.

EXAMPLES 17B to 29B

In each run, a glass reactor was charged with 1.9 parts of bisphenol A-type epoxy resin having an epoxy equivalent of 190 g/eq. and each of the N-oxazolines, component (C) and the catalyst shown in Table 8 in the indicated amounts. The mixture was heated to each of the temperatures shown in Table 8 after the inside of the glass vessel was purged with nitrogen at room temperature. The reaction mixture first dissolved uniformly, and then cured in each of the time periods indicated in Table 8 to a colorless to brown resin.

The resulting resins had no foam and were insoluble in acetone and other organic solvents. The heat-distortion temperature of the resulting resin shown in Table 8 demonstrate the high heat resistance of these resins.

TABLE 8

| Example | N-oxazoline (parts) | Component (C) (parts) | Catalyst (parts) | Reaction temperature (°C.) | Curing time | Heat distortion temperature (°C.) |
|---|---|---|---|---|---|---|
| 17B | N,N'-bis(2-oxazolinyl)-m-xylylenediamine (0.69) | 4,4'-methylene-dianiline (0.25) | ethyl p-toluenesulfonate (0.038) | 175 | 49 sec. | 160 |
| 18B | N,N'-bis(2-oxazolinyl)-m-xylylenediamine (1.37) | 4,4'-methylene-dianiline (0.79) | ethylbenzenesulfonate (0.11) | 175 | 32 sec. | 128 |
| 19B | N,N'-bis(2-oxazolinyl)-m-xylylenediamine (0.46) | hexamethylenediamine (0.10) | salicylic acid (0.038) | 200 | 1 min. 34 sec. | 130 |
| 20B | N,N'-bis(2-oxazolinyl)-m-xylylenediamine (0.69) | Tamanol 759* (0.53) | none | 150 | 1 min. 45 sec. | 130 |
| 21B | N,N'-bis(2-oxazolinyl)-m-xylylenediamine (0.69) | tetrahydrophthalic anhydride (0.38) | methylbenzenesulfonate (0.035) tris(dimethylaminomethyl)phenol (0.057) | 175 | 1 min. 43 sec. | 110 |
| 22B | N,N'-bis(2-oxazolinyl)-m-xylylenediamine (0.69) | bisphenol A (0.57) | none | 150 | 1 min. 53 sec. | 125 |
| 23B | N,N'-bis(2-oxazolinyl)-m-xylylenediamine (1.37) | bisphenol A (2.28) | benzyldimethylamine (0.036) | 150 | 1 min. 5 sec. | 120 |
| 24B | N,N'-bis(2-oxazolinyl)-m-xylylenediamine (1.37) | bisphenol A (1.14) | benzyldimethylamine (0.036) | 175 | 1 min. 35 sec. | 145 |
| 25B | N,N'-bis(2-oxazolinyl)-m-xylylenediamine (2.74) | bisphenol A (2.28) | none | 175 | 46 sec. | 140 |
| 26B | 1,3-bis(2-oxazolinyl)-aminomethyl)cyclohexane (0.71) | 4,4'-diaminodiphenylsulfone (0.30) | diethyl sulfate (0.031) | 175 | 3 min. 25 sec. | 163 |
| 27B | 1,3-bis(2-oxazolinyl)-aminomethyl)cyclohexane (0.49) | hexamethylenediamine (0.11) | salicylic acid (0.030) | 200 | 3 min. 10 sec. | 125 |
| 28B | 1,3-bis(2-oxazolinyl)- | bisphenol A | none | 175 | 2 min. | 141 |

TABLE 8-continued

| Example | N-oxazoline (parts) | Component (C) (parts) | Catalyst (parts) | Reaction temperature (°C.) | Curing time | Heat distortion temperature (°C.) |
|---|---|---|---|---|---|---|
| | aminomethyl)cyclohexane (0.40) | (1.14) | | | 58 sec. | |
| 29B | 1,3-bis(2-oxazolinyl)-aminomethyl)cyclohexane (0.71) | Tamanol 759* (0.50) | none | 150 | 3 min. 42 sec. | 123 |

*a tradename for phenol novolak produced by Arakawa Chemical Industries, Ltd.

EXAMPLES 30B to 35B

In each run, a glass vessel was charged with 1.8 parts of phenol novolak-type epoxy resin having an epoxy equivalent of 179 g/eq. and each of the N-oxazolines, component (C) and the catalyst shown in Table 9 in the amounts indicated. After purging the inside of the glass vessel with nitrogen, the mixture was heated to each of the temperatures shown in Table 9. The reaction mixture first dissolved uniformly and cured in each of the time periods shown in Table 9 to a colorless to brown resin.

The resulting resins had no foam and were insoluble in acetone and other organic solvents. The heat distortion temperatures of the resins shown in Table 9 demonstrate their excellent heat resistance.

tion temperatures of the resulting resins shown in Table 10 demonstrated their high heat resistance.

TABLE 10

| Example | Poly(N-oxazoline) (parts) | Curing time | Heat distortion temperature (°C.) |
|---|---|---|---|
| 36B | N,N'-bis(2-oxazolinyl)-m-xylylenediamine (0.69) | 5 min. 45 sec. | 155 |
| 37B | 1,3-bis(2-oxazolinyl-aminomethyl)cyclohexane (0.71) | 7 min. 22 sec. | 143 |

EXAMPLES 38B to 41B

TABLE 9

| Example | N-oxazoline (parts) | Component (C) (parts) | Catalyst (parts) | Reaction temperature (°C.) | Curing time | Heat distortion temperature (°C.) |
|---|---|---|---|---|---|---|
| 30B | N,N'-bis(2-oxazolinyl)-m-xylylenediamine (0.69) | 4,4'-methylenedianiline (0.25) | ethyl p-toluenesulfonate (0.025) | 175 | 1 min. 15 sec. | 168 |
| 31B | N,N'-bis(2-oxazolinyl)-m-xylylenediamine (1.37) | bisphenol A (1.14) | benzyldimethylamine (0.030) | 175 | 1 min. 59 sec. | 153 |
| 32B | N,N'-bis(2-oxazolinyl)-m-xylylenediamine (0.69) | hexahydrophthalic anhydride (0.39) | ethylbenzenesulfonate (0.032) tris(dimethylaminomethyl)phenol (0.042) | 175 | 2 min. 23 sec. | 121 |
| 33B | 1,3-bis(2-oxazolinyl-aminomethyl)cyclohexane (0.71) | 4,4'-methylenedianiline (0.25) | methyl p-toluenesulfonate (0.030) | 175 | 3 min. 52 sec. | 164 |
| 34B | 1,3-bis(2-oxazolinyl-aminomethyl)cyclohexane (0.49) | hexamethylenediamine (0.10) | salicylic acid (0.028) | 200 | 3 min. 48 sec. | 132 |
| 35B | 1,3-bis(2-oxazolinyl-aminomethyl)cyclohexane (0.71) | Tamanol 759* (0.50) | none | 175 | 2 min. 32 sec. | 131 |

*a tradename for phenol novolak produced by Arakawa Chemical Industries, Ltd.

EXMMPLES 36B and 37B

In each run, a glass vessel was charged with each of the N-oxazolines shown in Table 10 in the indicated amount, 1.85 parts of a product obtained by treating Epikote 815 (a product of Shell Chemical Co.) with 1 phr of methylene diisocyanate at 50° C. for 5 hours, and 0.44 part of tolylene diisocyanate (80% of the 2,4-form and 20% of the 2,6-form). After the inside of the glass vessel was purged wsith nitrogen, the mixture was heated to 150° C. The reaction mixture first dissolved uniformly, and then cured in each of the time periods indicated in Table 10 to a colorless resin.

The resulting resins had no foam and were insoluble in acetone and other organic solvents. The heat distor- In each run, a glass vessel was charged with each of the poly(N-oxazoline)s shown in Table 11 and component (C) shown in Table 11 in the indicated amounts, 1.9 parts of bisphenol A-type epoxy resin having an epoxy equivalent of 190 g/eq., 0.27 part of 2,2'-m-phenylenebis(2-oxazoline) and 0.013 part of methyl p-toluenesulfonate. After the inside of the glass vessel was purged with nitrogen at room temperature, the mixture was heated to each of the temperatures shown in Table 11. The reaction mixture first dissolved uniformly, and then cured in each of the time periods indicated in Table 11 to a pale yellow to orange resin.

The resulting resin had no foam and were insoluble in acetone and other organic solvents. The heat distortion temperatures of the resulting resins shown in Table 11 demonstrate their high heat resistance.

TABLE 11

| Example | Poly(N-oxazoline) (parts) | Component (C) (parts) | Reaction temperature (°C.) | Curing time | Heat distortion temperature (°C.) |
|---|---|---|---|---|---|
| 38B | N,N'-bis(2-oxazolinyl)-m-xylylenediamine (0.69) | 4,4'-methylene-dianiline (0.17) | 150 | 1 min. 54 sec. | 150 |
| 39B | N,N'-bis(2-oxazolinyl)-m-xylylenediamine (0.69) | Tamanol 759* (0.18) | 200 | 35 sec. | 145 |
| 40B | 1,3-bis(2-oxazolinyl-aminomethyl)cyclohexane (0.71) | 4,4'-methylene-dianiline (0.17) | 150 | 2 min. 20 sec. | 143 |
| 41B | 1,3-bis(2-oxazolinyl-aminomethyl)cyclohexane (0.71) | Tamanol 759* (0.18) | 200 | 1 min. 15 sec. | 139 |

*a tradename for phenol novolak produced by Arakawa Chemical Industries, Ltd.

EXAMPLE 42B

A liquid A composed of 43.4 parts of N,N'-bis(2-oxazolinyl)-m-xylylenediamine, 70 parts of bisphenol A-type epoxy resin having an epoxy equivalent of 190 g/eq. and 1.1 parts of benzyldimethylamine, and a liquid B composed of 36.1 parts of bisphenol A and 50 parts of bisphenol A-type epoxy resin having an epoxy equivalent of 190 g/eq. were prepared by heat melting.

The liquids A and B were injected into a mixing head heated at 140° C. and mixed, and immediately then filled into a mold kept at 150° C. to allow them to react for 10 minutes. The resulting molded article was transparent, foam-free and tough, and had a heat distortion temperature of 125° C.

EXAMPLES 43B and 44B

In each run, a glass vessel was charged with each of the poly(N-oxazoline)s shown in Table 12 in the indicated amount and 0.98 part of N,N,N',N'-tetraglycidyl-methylenedianiline having an epoxy equivalent of 106 g/eq. After the inside of the glass vessel was purged with nitrogen at room temperature, the mixture was heated to 150° C. The reaction mixture first dissolved uniformly, and then, in each of the time periods indicated in Table 12, cured to a yellow to brown resin.

The resulting resins had not foam and were insoluble in acetone and other organic solvents. The heat distortion temperatures of the resulitng resins shown in Table 12 demonstrate their high heat resistance.

TABLE 12

| Example | Poly(N-oxazoline) (parts) | Curing time | Heat distortion temperature (°C.) |
|---|---|---|---|
| 43B | N,N'-bis(2-oxazolinyl)-m-xylylenediamine (1.52) | 42 sec. | 189 |
| 44B | 1,3-bis(2-oxazolinyl-aminomethyl)cyclohexane (1.55) | 1 min. 20 sec. | 181 |

EXAMPLES 1C to 3C AND COMPARATIVE EXAMPLE 1C

In each run, a glass vessel was charged with each of the poly(N-cyclic iminoether)s shown in Table 13 in the indicated amount and 1.13 parts of bisphenol A. After the inside of the glass vessel was purged with nitrogen at room temperature, the mixture was heated to 150° C. The reaction mixture first dissolved uniformly, and then in each of the time periods indicated in Table 13, cured to a colorless to pale yellow resin. The resulting resins were tough and were insoluble in acetone and other organic solvents.

For comparison, the above procedure was repeated except that 2,2'-m-phenylenebis(2-oxazoline) was used instead of the poly(N-cylclic iminoether). No reaction occurred, and it was found that the reactivity of the poly(N-cyclic iminoether) was very high.

The heat distortion temperatures of the resulting resins shown in Table 13 demonstrated their high heat resistance.

TABLE 13

| Example | Cyclic iminoether (parts) | Curing time | Heat-distortion temperature (°C.) |
|---|---|---|---|
| 1C | N,N'-bis(2-oxazolinyl)-m-xylylenediamine (1.37) | 57 sec. | 130 |
| 2C | 1,3-bis(2-oxazolinyl-aminomethyl)cyclohexane (1.39) | 1 min. 17 sec. | 122 |
| 3C | N,N'-bis(2-oxazolinyl)-hexamethylenediamine (1.27) | 1 min. 3 sec. | 105 |
| Comparative Example 1C | 2,2'-m-phenylenebis-(2-oxazoline) (1.08) | did not cure. | |

EXAMPLE 4C and COMPARATIVE EXAMPLE 2C

A glass vessel was charged with 1.27 parts of N,N'-bis(2-oxazolinyl)hexamethylenediamine and 0.44 part of resorcinol. After the inside of the glass vessel was purged with nitrogen at room temperature, the mixture was heated to 150° C. The reaction mixture first dissolved uniformly, and then cured in 25 seconds to a colorless resin. The resulting resin was insoluble in acetone and other organic solvents and had a heat distortion temperature of 80° C.

For comparison, the above procedure was repeated except that 1.08 parts of 2,2'-m-phenylenebis(2-oxazoline) was used instead of N,N'-bis(2-oxazolinyl)hexamethylenediamine. No curing occurred, and it was found that the reactivity of the poly(N cyclic iminoether) is very high.

EXAMPLE 5C

A glass vessel was charged with 1.42 parts of N,N'-bis(2-oxazolinyl)-m-xylylenediamine and 1.09 parts of "TAMANOL" (a product of Arakawa Chemical Industires, Ltd.). After the glass vessel was purged with nitrogen at room temperature, the mixture was heated to 150° C. The reaction mixture first dissolved uniformly and then cured in 29 seconds to a yellow resin. The resulting resin was insoluble in acetone and other organic solvents and had a heat distortion temperature of 168° C. showing high heat resistance.

EXAMPLES 1D and 2D AND COMPARATIVE EXAMPLE 1D

In each run, a glass vessel was charged with each of the N-oxazolines shown in Table 14 in the indicated amount, 10 parts of an unsaturated polyester synthesized from maleic anhydride, isophthalic acid and propylene glycol (viscosity (measured at 25° C.; containing 40% of styrene monomer): 6.2 stokes; acid value: 70.0 mg KOH/g; the amount of the unsaturated bond measured by the dodecyl mercaptan method: 0.258 mol/g), and 10 parts of styrene. The compounds were uniformly dissolved by heating, and each of the catalysts shown in Table 14 in the indicated amount was added and well mixed. The resulting mixture was injected into a mold heated at 100° C. The reaction mixture cured in each of the time periods shown in Table 14. The reaction mixture was left to stand in the mold for 10 minutes and then taken out. A pale yellow molded plate free from cracking was obtained. The heat distortion temperatures of the resulting molded plates are shown in Table 14.

For comparison, the above procedure was repeated except that the N-oxazoline was not used. The molded plate developed cracking. This shows that the addition of the N-oxazoline improved moldability.

The heat-distortion temperatures of the resulting molded plates given in Table 14 shows that the addition of the N-oxazoline improved heat resistance.

TABLE 14

| Example | N-oxazoline (parts) | Catalyst (parts) | Curing time | Property of the molded article | Heat distortion temperature (°C.) |
|---|---|---|---|---|---|
| 1D | N,N'-bis(2-oxazolinyl)-m-xylylenediamine (1.55) | Kayaester 0-50* (0.4) Percadox 14* (0.2) diethyl sulfate (0.05) | 28 sec. | no cracking | 135 |
| 2D | 1,3-bis(2-oxazolinyl-aminomethyl)cyclohexane (1.58) | Kayaester 0-50* (0.4) Percadox 14* (0.2) diethyl sulfate (0.05) | 35 sec. | no cracking | 132 |
| Comp. Ex. 1D | none | Kayaester 0-50* (0.4) Percadox 14* (0.2) | 19 sec. | cracking occurred | 120 |

*products of Kayaku Noury Co.

EXAMPLES 3D AND COMPARATIVE EXAMPLE 2D

In each run, a glass vessel was charged with each of the N-oxazolines shown in Table 15 in the indicated amount, 10 parts of an unsaturated polyester synthesized from maleic anhydride, isophthalic acid and propylene glycol [viscosity (measured at 25° C., containing 40% of styrene monomer): 5.6 stokes; acid value: 38 mg KOH/g; the amount of an unsaturated bond measured by the dodecyl mercaptan method: 0.295 mol/g] and 10 parts of styrene. The mixture was heated to form a uniform solution. Then, each of the catalysts shown in Table 15 in the indicated amount was added and mixed well. The mixture was injected into a mold kept at 100° C. It cured in the time periods indicated in Table 15. The reaction mixture was left to stand in the mold for 10 minutes and then taken out to obtain a pale yellow crack-free molded plate. The heat distortion temperatures of the resulitng molded plates are shown in Table 15.

For comparison, the above procedure was repeated except that the N-oxazoline was not used. Cracking occurred in the molded plate, and this showed that the addition of the N-oxazoline improved moldability. The heat distortion temperatures of the resulting molded plates are shown in Table 15. This shows that the addition of the N-oxazoline improved heat resistance.

TABLE 15

| Example | N-oxazoline (parts) | Catalyst (parts) | Curing time | Property of the molded article | Heat distortion temperature (°C.) |
|---|---|---|---|---|---|
| 3D | N,N'-bis(2-oxazolinyl)-m-xylylenediamine (1.55) | Kayaester 0-50* (0.4) dimethyl sulfate (0.05) | 24 sec. | no cracking | 122 |
| 4D | 1,3-bis(2-oxazolinyl-aminomethyl)cyclohexane (1.58) | Kayaester 0-50* (0.4) dimethyl sulfate (0.05) | 35 sec. | no cracking | 119 |
| Comp. Ex. 2D | none | Kayaester 0-50* (0.4) | 34 sec. | cracking occurred | 104 |

*products of Kayaku Noury Co.

EXAMPLES 5D to 7D

In each run, a glass vessel was charged with each of the N-oxazolines shown in Table 16 in the amount indicated, 10 parts of an unsaturated polyester synthesized from maleic anhydride, isophthalic acid and propylene glycol [viscosity (measured at 25° C.; containing 40% of styrene monomer): 5.6 stokes; acid value: 58.1 mg KOH/g; the amount of the unsaturated bond measured by the dodecyl mercaptan method: 0.316 mol/g] and 10 parts of styrene. The mixture was heatd to form a uniform solution. The catalyst shown in Table 16 in the indicated amount was added and well mixed, and the glass vessel was immersed in an oil bath kept at 100° C. The reaction mixture cured in each of the time period shown in Table 16 to a pale yellow to brown resin. The heat distortion temperatures of the resulting resins shown in Table 16 demonstrated their excellent heat resistance.

TABLE 16

| Example | N-oxazoline (parts) | Catalyst (parts) | Curing time | Heat distortion temperature (°C.) |
|---|---|---|---|---|
| 5D | N,N'-bis(2-oxa-zolinyl)-m-xylylenediamine (1.55) | Kayaester 0-50* (0.4) | 22 sec. | 145 |
| 6D | N,N'-bis(2-oxa-zolinyl)-m-xylylenediamine (6.20) | Kayaester 0-50* (0.4) ethyl p-toluene-sulfonate (0.2) | 38 sec. | 128 |
| 7D | 1,3-bis(2-oxa-zolinylamino-methyl)cyclo-hexane (1.58) | Kayaester 0-50* (0.4) | 34 sec. | 139 |

*a product of Kayaku Noury Co.

EXAMPLES 8D and 9D

In each run, a glass vessel was charged with 0.15 part of N,N'-bis(2-oxazolinyl)-N,N'-bis(3-butoxy-2-hydroxypropyl)-m-xylylenediamine, 0.5 part of each of the unsaturated polyesters shown in Table 17 and 0.5 part of styrene. The compounds were heated to form a uniform solution, and the catalyst shown in Table 17 in the indicated amount was added and well mixed. The glass vessel was then immersed in an oil bath kept at 100° C. The reaction mixture cured in each of the time periods shown in Table 17 to a pale yellow crack-free resin. The heat distortion temperatures of the resulting resins shown in Table 17 demonstrated their excellent heat resistance.

TABLE 17

| Example | Unsaturated polyester | Catalyst (parts) | Curing time | Heat distortion temperature (°C.) |
|---|---|---|---|---|
| 8D | unsaturated polyester used in Example 1D | Kayaester 0-50* (0.02) Percadox 14* (0.01) diethyl-sulfuric acid (0.005) | 18 sec. | 127 |
| 9D | unsaturated polyester used in Example 5D | Kayaester 0-50* (0.02) Percadox 14* (0.01) diethyl-sulfuric acid (0.005) | 21 sec. | 132 |

*products of Kayaku Noury Co.

EXAMPLES 10D to 15D

In each run, a glass vessel was charged with 5.0 parts of N,N'-bis(2-oxazolinyl)-m-xylylenediamine, a solution prepared from the unsaturated polyester used in Example 5D and styrene in a weight ratio of 1:1 in the amount indicated in Table 18, and component (D) in the indicated amount in Table 18. These compounds were heated to form a uniform solution. The catalyst shown in Table 18 was added in the amount indicated and well mixed. The glass vessel was then immersed in an oil bath kept at 100° C. The reaction mixture cured in each of the time periods indicated in Table 18 to a pale yellow to brown resin. The heat distortion temperature of the resulting resins shown in Table 18 demonstrate their excellent heat resistance.

TABLE 18

| Example | Amount of the unsaturated polyester/ styrene (parts) | Component (D) (parts) | Catalyst (parts) | Curing time | Heat distortion temperature (°C.) |
|---|---|---|---|---|---|
| 10D | 26.3 | 4,4'-methyl-enedianiline (2.9) | Kayaester 0-50* (0.26) methyl p-toluene-sulfonate (0.40) | 28 sec. | 150 |
| 11D | 7.8 | 4,4'-methyl-enedianiline (2.8) | Kayaester 0-50* (0.08) ethylbenzene-sulfonate (0.39) | 1 min. 35 sec. | 118 |
| 12D | 27.8 | bisphenol A (3.3) | Kayaester 0-50* (0.28) | 49 sec. | 128 |
| 13D | 23.8 | adipic acid (2.1) | Kayaester 0-50* (0.24) p-toluene-sulfonate acid (0.25) | 18 sec. | 128 |
| 14D | 21.7 | maleic anhydride (1.5) | Kayaester 0-50* (0.22) ethyl p-toluene-sulfonate (0.23) | 7 sec. | 170 |
| 15D | 23.8 | cyclo-hexane-dimethanol (2.1) | Kayaester 0-50* (0.24) methyl-benzene-sulfonate (0.36) | 29 sec. | 120 |

*a product of Kayaku Noury Co.

EXAMPLES 16D to 20D

In each run, a glass vessel was charged with 5.1 parts of 1,3-bis(2-oxazolinylaminomethyl)cyclohexane, a solution prepared from styrene and the unsaturated polyester used in Example 5D in a weight ratio of 1:1 and component (D) shown in Table 19 in the amounts indicated. The mixture was heated to form a uniform mixture. The catalyst shown in Table 19 was added in the indicated amount and well mixed. The glass vessel was immmersed in an oil bath kept at 100° C. The reaction mixture cured in each of the time periods indicated in Table 19 to a pale yellow to brown resin. The heat distortion temperatures of the resulting resins shown in Table 19 demonstrate their excellent heat resistance.

TABLE 19

| Example | Amount of the unsaturated polyester/ styrene (parts) | Component (D) (parts) | Catalyst (parts) | Curing time | Heat distortion temperature (°C.) |
|---|---|---|---|---|---|
| 16D | 26.3 | 4,4'-methylenedianiline (2.9) | Kayaester O-50* (0.26) ethyl p-toluenesulfonate (0.40) | 32 sec. | 142 |
| 17D | 27.8 | bisphenol A (3.3) | Kayaester O-50* (0.28) | 56 sec. | 122 |
| 18D | 23.8 | adipic acid (2.1) | Kayaester O-50* (0.24) benzenesulfonic acid (0.25) | 29 sec. | 121 |
| 19D | 21.7 | maleic anhydride (1.5) | Kayaester O-50* (0.22) methyl p-toluenesulfonate (0.23) | 18 sec. | 165 |
| 20D | 23.8 | cyclohexanedimethanol (2.1) | Kayaester O-50* (0.24) p-toluenesulfonic acid (0.36) | 42 sec. | 118 |

*a product of Kayaku Noury Co.

EXAMPLE 21D

A liquid A composed of 50 parts of the unsaturated polyester used in Example 5D, 35 parts of styrene and 0.39 part of diethylsulfuric acid and a liquid B composed of 7.8 parts of N,N'-bis(2-oxazolinyl)-m-xylylenediamine, 15 parts of styrene, 1 part of Kayaester O-50 (a product of Kayaku Noury Co.) and 1 part of Percadox 14 (a product of Kayaku Noury Co.) were prepared by heat melting. The liquids A and B were injected into a mixing head kept at 90° C. and mixed, and immediately then, filled into a mold heated at 100° C. to allow it to react for 10 minutes. The resulting molded article was transparent and free from cracking and had a heat distortion temperature of 135° C.

EXAMPLES 22D and 23D

In each run, a glass vessel was charged with each of the N-oxazolines shown in Table 20 in the indicated amount, 1.0 part of the unsaturated polyester used in Example 5D, 1.0 part of styrene, 0.22 part of 2,2'-m-phenylenebis(2-oxazoline) and 0.16 part of 4,4'-methylenedianiline. The mixture was heated to form a uniform solution. Then, 0.04 part of Kayaester O-50 (a product of Kayaku Noury Co.), 0.02 part of Percadox 14 (a product of Kayaku Noury Co.), and 0.02 part of ethyl p-toluenesulfonate were added and well mixed. The glass vessel was immersed in an oil bath kept at 100° C. The reaction mixture cured in each of the time periods indicated in Table 19 to a brown to reddish brown resin. The heat distortion temperatures of the resulting resins shown in Table 20 demonstrate their excellent heat resistance.

TABLE 20

| Example | N-oxazoline (parts) | Curing time | Heat distortion temperature (°C.) |
|---|---|---|---|
| 22D | N,N'-bis(2-oxazolinyl)-m-xylylenediamine (0.38) | 46 sec. | 157 |
| 23D | 1,3-bis(2-oxazolinylaminomethyl)cyclohexane (0.39) | 1 min. 2 sec. | 151 |

EXAMPLES 1E and 2E AND COMPARATIVE EXAMPLE 1E

In each run, a glass vessel was charged with each of the poly(N-cyclic iminoether)s shown in Table 21 in the indicated amount, 0.98 part of polyethylene glycol having an average molecular weight of 300 and 0.74 part of bisphenol A. With deaeration, the mixture was heated to form a uniform solution. The temperature of the reaction mixture was lowered to below 70° C., 0.08 part of ethyl p-toluenesulfonate was added and dissolved. Furthermore, 1.14 parts of tolylene diisocyanate (80% of the 2,4-form and 20% of the 2,6-form) was added and uniformly dissolved. The solution was deaerated and then reacted in an oil bath kept at 150° C. The reaction mixture cured in each of the time periods indicated in Table 21 to a transparent resin. The resulting molded article was heat-treated at 175° C. for 1 hour. The heat distortion temperatures of the heat-treated products are shown in Table 21.

For comparison, the above procedure was repeated except that 0.99 part of the above tolylene diisocyanate, 1.57 parts of polyethylene glycol and 0.02 part of di-n-butyltin dilaurate were used as the materials. The resulting molded article was rubbery at room temperature. It was thus seen that the resins obtained in accordance with this invention have high heat resistance.

TABLE 21

| Example | Poly(N-cyclic iminoether) (parts) | Curing time | Heat distortion temperature (°C.) |
|---|---|---|---|
| 1E | N,N'-bis(2-oxazolinyl)-m-xylylenediamine (0.89) | 3 min. 5 sec. | 125 |
| 2E | 1,3-bis(2-oxazolinylaminomethyl)cyclohexane (0.91) | 3 min. 18 sec. | 120 |

EXAMPLES 3E and 4E

In each run, a glass vessel was charged with each of the poly(N-cyclic iminoether)s shown in Table 22 in the indicated amount, 0 65 part of polyethylene glycol having an average molecular weight of 200 and 0.74 part of bisphenol A. With deaeration, the mixture was heated to form a uniform solution. The temperature of the reaction mixture was lowered to below 70° C., and 0.07 part of methyl p-toluenesufonate was added and dissolved. Furthermore, 1.13 parts of 4,4'-methylenebis(-phenyl isocyanate) was added and uniformly dissolved. After deaeration, the solution was reacted in an oil bath kept at 150° C. The reaction mixture cured in each of the time periods shown in Table 22 to a transparent resin.

The resulting molded articles were heat-treated at 175° C. for 1 hour. The heat distortion temperatures of the heat-treated products are shown in Table 22. It is seen that they have relatively high heat resistance.

TABLE 22

| Example | Poly(N-cyclic iminoether) (parts) | Curing time | Heat distortion temperature (°C.) |
|---|---|---|---|
| 3E | N,N'-bis(2-oxazolinyl)-m-xylylenediamine (0.89) | 3 min. 12 sec. | 128 |
| 4E | 1,3-bis(2-oxazolinyl-aminomethyl)cyclohexane (0.91) | 3 min. 30 sec. | 124 |

EXAMPLES 5E and 6E

In each run, a glass vessel was charged with each of the poly(N-cyclic iminoether)s shown in Table 23 in the indicated amount, 1.32 parts of polyethylene glycol having an average molecular weight of 300 and 0.13 part of TAMANOL 759 (a product of Arakawa Chemical Industries, Ltd.). With deaeration, the mixture was heated to form a uniform solution. The temperature of the reaction mixture was lowered to below 70° C., and 0.02 part of ethyl benzenesulfonate was added and dissolved. Furthermore, 0.89 part of tolylene diisocyanate (80% of the 2,4-form and 20% of the 2,6-form) was added and dissolved uniformly. The solution was deaerated, and reacted in an oil bath at 150° C. The reaction mixture cured in each of the time periods shown in Table 23 to a transparent resin. The heat distortion temperatures of the resulting molded articles shown in Table 23 demonstrate their high heat resistance.

TABLE 23

| Example | Poly(N-cyclic iminoether) (parts) | Curing time | Heat distortion temperature (°C.) |
|---|---|---|---|
| 5E | N,N'-bis(2-oxazolinyl)-m-xylylenediamine (0.17) | 1 min. 25 sec. | 85 |
| 6E | 1,3-bis(2-oxazolinyl-aminomethyl)cyclohexane (0.17) | 1 min. 32 sec. | 78 |

EXAMPLES 7E and 8E

In each run, a glass vessel was charged with each of the poly(N-cyclic iminoether)s shown in Table 24 in the indicated amount, 1.10 parts of polyethylene glycol having an average molecular weight of 300, 0.16 part of diethyldiaminotoluene and 0.15 part of bisphenol A. With deaeration, the mixture was heated to form a uniform solution. The temperature of the reaction mixture was lowered to below 60° C., and 0.02 part of ethyl p-toluenesulfonate was added and dissolved. Furthermore, 0.91 part of tolylene diisocyanate (80% of the 2,4-form and 20% of the 2,6-form) was added and dissolved uniformly. The solution was deaerated, and reacted in an oil bath kept at 150° C. The reaction mixture cured in each of the time periods shown in Table 24 to a transparent resin. The heat distortion temperatures of the resulting molded articles shown in Table 2 demonstrate their high heat resistance.

TABLE 24

| Example | Poly(N-cyclic iminoether) (parts) | Curing time | Heat distortion temperature (°C.) |
|---|---|---|---|
| 7E | N,N'-bis(2-oxazolinyl)-m-xylylenediamine (0.18) | 8 sec. | 92 |
| 8E | 1,3-bis(2-oxazolinyl-aminomethyl)cyclohexane (0.18) | 9 sec. | 83 |

We claim:
1. A poly(N-cyclic iminoether) compound represented by the following formula (I)-A

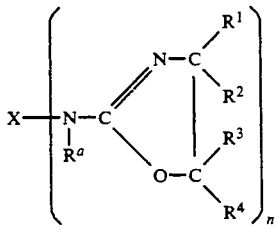

wherein $R^1$, $R^2$, $R^3$ and $R^4$ are identical or different and each represents a hydrogen atom, an alkyl group having 1 to 3 carbon atoms, a benzyl group, a phenyl group or a tolyl group, $R^a$'s are identical or different and each represents a hydrogen atom or a monovalent hydrocarbon group which may be interrupted by a heteroatom, n is an integer of 2 to 10, and X is an n-valent hydrocarbon group selected from the group consisting of an alkylene group having 1 to 15 carbon atoms, an alicyclic hydrocarbon group having from 6 to 15 carbon atoms, a monocyclic or bicyclic aromatic hydrocarbon group having from 6 to 15 carbon atoms, a monocyclic or bicyclic aromatic hydrocarbon group interrupted by a heteroatom,

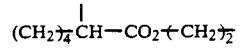

or

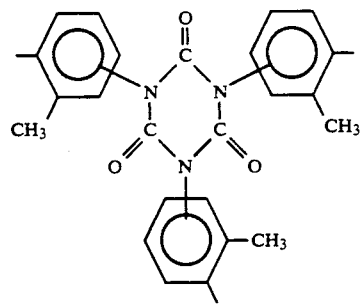

and

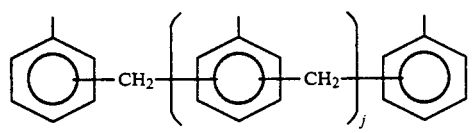

wherein j is a number of 1 to 8; and
when n is 2, X may be a direct bond or a group of the formula (a)

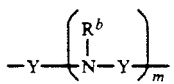 (a)

wherein Y is a divalent hydrocarbon group which may be interrupted by a heteroatom, m is an integer of 1 to 10, with the proviso that when m is an integer of 2 to 10, two or more $R^b$'s may be the same or different, and $R^b$ represents a hydrogen atom or a group of the formula

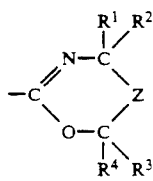

wherein $R^1$, $R^2$, $R^3$ and $R^4$ are as defined above, and Z is a direct bond or group of the formula

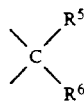

wherein $R^5$ and $R^6$ are identical or different and each represents a hydrogen atom, an alkyl group having 1 to 3 carbon atoms, a benzyl group, a phenyl group or a tolyl group.

2. A poly(N-cyclic iminoether) compound of claim 1 wherein X represents methylene, ethylene, trimethylene, tetramethylene, hexamethylene, 2,2-dimethylpentamethylene, cyclohexylene, 4-methyl-1,3-cyclohexylene,

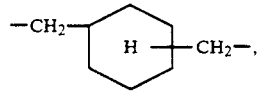

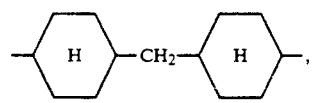

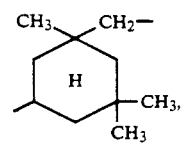

2,4-tolylene, 2,6-tolylene a mixture of 2,4- and 2,6-tolylene, m-xylylene, p-xylylene,

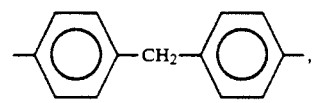

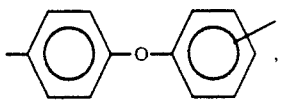

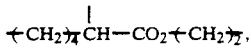

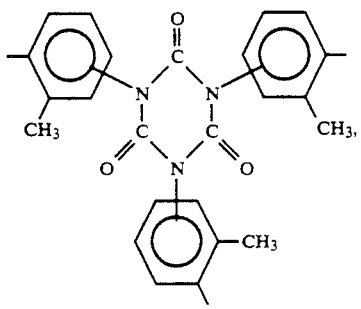

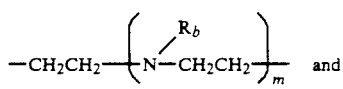

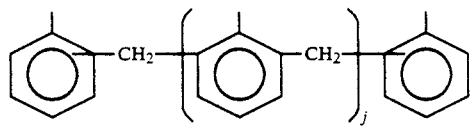

where $R^b$ and m are as defined and j is a number of 1 to 8.

3. A poly(N-cyclic iminoether) compound represented by the following formula (I)-B

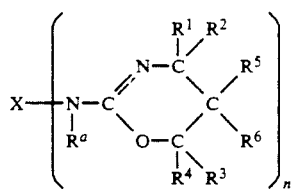 (I)-B wherein n is an integer of 2 to 10,

X is an n-valent hydrocarbon group which may be interrupted by a hetero atom, or when n is 2, X may also represent a direct bond or a group of the formula (a)

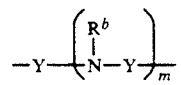 (a)

in which $R^b$ represents a hydrogen atom or a group of the following formula

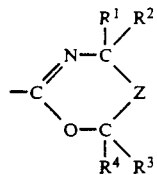

$R^a$'s are identical or different and each represents a hydrogen atom or a monovalent hydrocarbon group which may be interrupted by a hetero atom, $R^1$, $R^2$, $R^3$ and $R^4$ are identical or different and each represents a hydrogen atoms, an alkyl group having 1 to 3 carbon atoms, a benzyl group, a phenyl group or a tolyl group, Z is a direct bond or a group of the formula

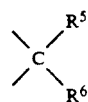

Y is a divalent hydrocarbon group which may be interrupted by a hetero atom, m is an integer of 1 to 10 with the proviso that when m is an integer of 2 to 10, two or more $R^b$'s may be identical or different, and $R^5$ and $R^6$ are identical or different and each represents a group selected from the groups defined by $R^1$.

4. A process for producing a poly(N-cyclic iminoether) compound represented by the following formula (I)-a

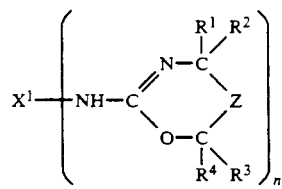

wherein $X^1$, $R^1$, $R^2$, $R^3$, $R^4$, Z and n are as defined below, which comprises (1) reacting a polyisocyanate compound represenered by the following formula

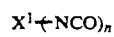

wherein $X^1$ represents an n-valent hydrocarbon group which may be interrupted by a hetero atom, and n is an integer of 2 to 10, with a haloalkylamine represented by the following formula

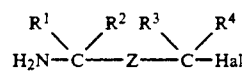

wherein Z represents a direct bond or a group of the following formula

$R^1$, $R^2$, $R^3$, $R^4$, $R^5$ and $R^6$ are identical or different and each represents hydrogen, alkyl having 1 to 3 carbon atoms, benzyl, phenyl or tolyl, and Hal represents a halogen atom, and (2) thereafter cyclizing the resulting polyurea compound.

5. A process for producing a poly(N-cyclic iminoether) compound represented by the following formula (I)

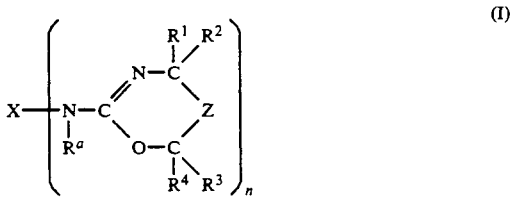

wherein $R^a$, $R^1$, $R^2$, $R^3$, $R^4$, Z and n are as defined below, X represents a direct bond or an n-valent hydrocarbon group which may be interrupted by a hetero atom, or when n is 2, X may also represent a group of the following formula (a)

in which Y is as defined below, $R^b$ represents a hydrogen atom or a group of the following formula

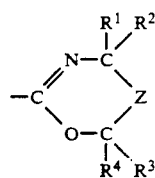

m is an integer of 1 to 10 with the proviso that when m is an integer of 2 to 10, two or more $R^b$'s may be identical or different, which comprises;

(1) reacting a polyamine compound represented by the following formula

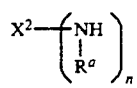

wherein n is an integer of 2 to 10, $X^2$ represents a direct bond or an n-valent hydrocarbon group which may be interrupted by a hetero atom, or when n is 2, $X^2$ may be a group of the following formula (a)'

in which Y represents a divalent hydrocarbon group which may be interrupted by a hetero atom, and m is an integer of 1 to 10, $R^a$'s are identical or different and each represents a hydrogen atom or a monovalent hydrocarbon group which may be interrupted by a hetero atom, with an alkyl isocyanate represented by the following formula

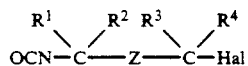

wherein Z is a direct bond or a group of the formula

$R^1$, $R^2$, $R^3$, $R^4$, $R^5$ and $R^6$ are identical or different and each represents hydrogen, alkyl of 1 to 3 carbon atoms, benzyl, phenyl or tolyl, and Hal represents a halogen atoms (2) thereafter cyclizing the resulting polyurea compound.

* * * * *